US012796944B2

(12) United States Patent
Williams et al.

(10) Patent No.: US 12,796,944 B2
(45) **Date of Patent: *Nov. 17, 2026**

(54) SYSTEMS AND METHODS FOR PERSONALIZED TREATMENT OF NEUROLOGICAL CONDITIONS USING IMPLANTABLE NEUROSTIMULATORS

(71) Applicant: The Board of Trustees of the Leland Stanford Junior University, Stanford, CA (US)

(72) Inventors: Nolan Williams, Stanford, CA (US); Keith Sudheimer, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 942 days.

This patent is subject to a terminal disclaimer.

(21) Appl. No.: 17/327,581

(22) Filed: May 21, 2021

(65) Prior Publication Data

US 2021/0378531 A1 Dec. 9, 2021

Related U.S. Application Data

(63) Continuation of application No. 16/215,519, filed on Dec. 10, 2018, now Pat. No. 11,013,423.
(Continued)

(51) Int. Cl.
*A61N 2/00* (2006.01)
*A61B 5/00* (2006.01)
(Continued)

(52) U.S. Cl.
CPC .......... *A61B 5/02405* (2013.01); *A61B 5/165* (2013.01); *A61B 5/4836* (2013.01);
(Continued)

(58) Field of Classification Search
CPC .......... A61N 2/004; A61N 2/006; A61N 2/02
See application file for complete search history.

(56) References Cited

U.S. PATENT DOCUMENTS

| | | | | |
|---|---|---|---|---|
| 7,747,318 B2 * | 6/2010 | John | .................... | A61B 8/0808 607/2 |
| 10,449,384 B2 | 10/2019 | Williams et al. | | |

(Continued)

FOREIGN PATENT DOCUMENTS

| | | |
|---|---|---|
| EP | 3737467 A2 | 11/2020 |
| GB | 2585282 A | 1/2021 |

(Continued)

OTHER PUBLICATIONS

A New Study to Treat Depression, https://www.youtube.com/watch?v=20Z2eHecvY4, Oct. 27, 2017, 1 page.

(Continued)

*Primary Examiner* — Christine H Matthews
(74) *Attorney, Agent, or Firm* — KPPB LLP

(57) ABSTRACT

Systems and methods for treatment of neurological conditions using implantable neurostimulators in accordance with embodiments of the invention are illustrated. One embodiment includes a method for treating neurological conditions, including obtaining image data of a patient's brain, where the image data describes neuronal activations within the patient's brain, determining a location on the patient's brain to implant a neurostimulator, and surgically implanting a neurostimulator at the location, and applying a stimulation protocol to the brain at the location using the neurostimulator to treat the neurological condition. An additional embodiment includes an implantable neurostimulator configured to apply an aTBS protocol to a patient's brain.

18 Claims, 13 Drawing Sheets

Related U.S. Application Data

(60) Provisional application No. 62/617,121, filed on Jan. 12, 2018.

(51) Int. Cl.

| | |
|---|---|
| ***A61B 5/024*** | (2006.01) |
| ***A61B 5/16*** | (2006.01) |
| ***A61N 2/02*** | (2006.01) |
| ***G01R 33/48*** | (2006.01) |
| ***G01R 33/565*** | (2006.01) |
| ***G16H 20/30*** | (2018.01) |
| *G16H 50/30* | (2018.01) |

(52) U.S. Cl.

CPC ............. *A61N 2/004* (2013.01); *A61N 2/006* (2013.01); *A61N 2/02* (2013.01); *G01R 33/4806* (2013.01); *G01R 33/4808* (2013.01); *G01R 33/565* (2013.01); *G16H 20/30* (2018.01); *A61B 5/681* (2013.01); *A61B 2576/026* (2013.01); *G16H 50/30* (2018.01)

(56) References Cited

U.S. PATENT DOCUMENTS

| | | | |
|---|---|---|---|
| 10,595,735 B2 | 3/2020 | Williams et al. | |
| 10,765,856 B2 | 9/2020 | Wong et al. | |
| 11,013,423 B2 | 5/2021 | Williams et al. | |
| 11,213,215 B2 | 1/2022 | Williams et al. | |
| 11,344,722 B2 | 5/2022 | Wong et al. | |
| 11,534,074 B2 | 12/2022 | Williams et al. | |
| 11,839,455 B2 | 12/2023 | Williams et al. | |
| 2006/0217781 A1 | 9/2006 | John | |
| 2007/0173901 A1 | 7/2007 | Reeve | |
| 2009/0105521 A1 | 4/2009 | Bentwich | |
| 2011/0224571 A1 | 9/2011 | Pascual-leone et al. | |
| 2011/0245633 A1 | 10/2011 | Goldberg et al. | |
| 2013/0137918 A1 | 5/2013 | Phillips et al. | |
| 2013/0281890 A1* | 10/2013 | Mishelevich ...... | A61N 1/36085 601/2 |
| 2014/0058279 A1 | 2/2014 | Shinba | |
| 2014/0206945 A1 | 7/2014 | Liao | |
| 2015/0119689 A1 | 4/2015 | Pascual-Leone et al. | |
| 2016/0008620 A1 | 1/2016 | Stubbeman | |
| 2016/0019693 A1 | 1/2016 | Silbersweig et al. | |
| 2016/0367804 A1 | 12/2016 | Peng et al. | |
| 2017/0249438 A1 | 8/2017 | Jain et al. | |
| 2019/0001129 A1 | 1/2019 | Rosenbluth et al. | |
| 2019/0216342 A1 | 7/2019 | Williams et al. | |
| 2019/0217112 A1 | 7/2019 | Williams et al. | |
| 2019/0217113 A1 | 7/2019 | Williams et al. | |
| 2019/0217116 A1 | 7/2019 | Williams et al. | |
| 2019/0336018 A1 | 11/2019 | Williams et al. | |
| 2020/0214581 A1 | 7/2020 | Williams et al. | |
| 2021/0353224 A1 | 11/2021 | Etkin et al. | |
| 2022/0202302 A1 | 6/2022 | Williams et al. | |
| 2023/0210388 A1 | 7/2023 | Williams et al. | |
| 2024/0065564 A1 | 2/2024 | Williams et al. | |

FOREIGN PATENT DOCUMENTS

| | | | |
|---|---|---|---|
| GB | 2585282 | B | 5/2022 |
| GB | 2602429 | A | 6/2022 |
| GB | 2602429 | B | 11/2022 |
| JP | 2011517962 | A | 6/2011 |
| JP | 2012177112 | A | 9/2012 |
| JP | 2021510572 | A | 4/2021 |
| JP | 7377546 | B2 | 11/2023 |
| JP | 2023181300 | A | 12/2023 |
| WO | 2015079439 | A1 | 6/2015 |
| WO | 2015153675 | A1 | 10/2015 |
| WO | 2017172487 | A1 | 10/2017 |
| WO | 2017189757 | A1 | 11/2017 |
| WO | 2019140303 | A2 | 7/2019 |
| WO | 2019140303 | A3 | 7/2019 |
| WO | 2020081609 | A1 | 4/2020 |

OTHER PUBLICATIONS

International Preliminary Report on Patentability for International Application No. PCT/US2019/013353, Report issued Jul. 14, 2020, Mailed Jul. 23, 2020, 7 Pgs.

International Search Report and Written Opinion for International Application No. PCT/US2019/013353, Search completed Jul. 31, 2019, Mailed Nov. 14, 2019, 13 Pgs.

Aguirre et al., "Age predicts low-frequency transcranial magnetic stimulation efficacy in major depression," Journal of Affective Disorders, vol. 130, No. 3, May 2011, Electronic Publication: Nov. 18, 2010, pp. 466-469.

Allen et al., "The stability of resting frontal electroencephalographic asymmetry in depression," Psychophysiology, vol. 41, No. 2, Mar. 2004, pp. 269-280.

Anderson et al., "Repetitive transcranial magnetic stimulation for treatment resistant depression: Re-establishing connections," Clinical Neurophysiology, vol. 127, No. 11, Nov. 2016, pp. 3394-3405.

Baeken et al., "Accelerated HF-rTMS in treatment-resistant unipolar depression: Insights from subgenual anterior cingulate functional connectivity," The World Journal of Biological Psychiatry, vol. 15, No. 4, Jan. 21, 2014, pp. 286-297.

Baeken et al., "Neurobiological mechanisms of repetitive transcranial magnetic stimulation on the underlying neurocircuitry in unipolar depression," Dialogues in Clinical Neuroscience, vol. 13, No. 1, Mar. 2011, pp. 139-145.

Baeken et al., "The Impact of Accelerated HF-rTMS on the Subgenual Anterior Cingulate Cortex in Refractory Unipolar Major Depression: Insights From 18FDG Pet Brain Imaging," Brain Stimulation, vol. 8, No. 4, Jul.-Aug. 2015, pp. 808-815.

Bakker et al., "rTMS of the dorsomedial prefrontal cortex for major depression: safety, tolerability, effectiveness, and outcome predictors for 10 Hz versus intermittent theta-burst stimulation," Brain Stimul, vol. 8, No. 2, 2015, pp. 208-215.

Berenyi et al., "Closed-Loop Control of Epilepsy by Transcranial Electrical Stimulation," Science, vol. 337, Aug. 10, 2012, pp. 735-737.

Berlim et al., "A systematic review and meta-analysis on the efficacy and acceptability of bilateral repetitive transcranial magnetic stimulation (rTMS) for treating major depression," Psychological Medicine, vol. 43, No. 11, Nov. 2013, Electronic Publication: Dec. 3, 2012, pp. 2245-2254.

Berlim et al., "Blinding integrity in randomized sham-controlled trials of repetitive transcranial magnetic stimulation for major depression: a systematic review and meta-analysis," International Journal of Neuropsychopharmacology, vol. 16, No. 5, Jun. 2013, Electronic Publication: Feb. 11, 2013, pp. 1173-1181.

Berlim et al., "Clinically Meaningful Efficacy and Acceptability of Low-Frequency Repetitive Transcranial Magnetic Stimulation (rTMS) for Treating Primary Major Depression: A Meta-Analysis of Randomized, Double-Blind and Sham-Controlled Trials," Neuropsychopharmacology, vol. 38, No. 4, Mar. 2013, Electronic Publication: Nov. 19, 2012, pp. 543-551.

Berlim et al., "High-Frequency Repetitive Transcranial Magnetic Stimulation Accelerates and Enhances the Clinical Response to Antidepressants in Major Depression: A Meta-Analysis of Randomized, Double-Blind, and Sham-Controlled Trials," Journal of Clinical Psychiatry, vol. 74, No. 2, Feb. 2013, pp. e122-e129.

Berlim et al., "Response, remission and drop-out rates following high- frequency repetitive transcranial magnetic stimulation (rTMS) for treating major depression: a systematic review and meta-analysis of randomized, double-blind and sham-controlled trials," Psychological Medicine, vol. 44, No. 2, Jan. 2014, Electronic Publication: Mar. 18, 2013, pp. 225-239.

Blumberger et al., "Effectiveness of theta burst versus high-frequency repetitive transcranial magnetic stimulation in patients with depression (Three-D): a randomised non-inferiority trial," The Lancet, vol. 391, No. 10131, Apr. 28, 2018, pp. 1683-1692.

(56) References Cited

OTHER PUBLICATIONS

Brakemeier et al., "Patterns of response to repetitive transcranial magnetic stimulation (rTMS) in major depression: Replication study in drug-free patients," Journal of Affective Disorders, vol. 108, No. 1-2, May 2008, pp. 59-70.
Camprodon et al., "Two Phases of V1 Activity for Visual Recognition of Natural Images," Journal of Cognitive Neuroscience, vol. 22, No. 6, Jun. 2010, pp. 1262-1269.
Cao et al., "Augmenting saturated LTP by broadly spaced episodes of theta-burst stimulation in hippocampal area CA1 of adult rats and mice," Journal of Neurophysiology, vol. 112, No. 8, Oct. 15, 2014, pp. 1916-1924.
Capocchi et al., "Theta burst stimulation is optimal for induction of LTP at both apical and basal dendritic synapses on hippocampal CA1 neurons," Brain Research, vol. 591, No. 2, Sep. 25, 1992, pp. 332-336.
Cardenas-Morales et al., "Exploring the after-effects of theta burst magnetic stimulation on the human motor cortex: A functional imaging study," Human Brain Mapping, vol. 32, No. 11, Nov. 2011, Electronic Publication: Dec. 22, 2010, pp. 1948-1960.
Cash et al., "Subgenual Functional Connectivity Predicts Antidepressant Treatment Response to Transcranial Magnetic Stimulation: Independent Validation and Evaluation of Personalization," Biological Psychiatry, Articles in Press, Jan. 19, 2019, 5 Pgs.
Cazzoli et al., "Theta burst stimulation reduces disability during the activities of daily living in spatial neglect," Brain, 135, Part 11, 2012, pp. 3426-3439.
Chalifoux et al., "GABAB Receptor Modulation of Voltage-Sensitive Calcium Channels in Spines and Dendrites," Journal of Neuroscience, vol. 31, No. 11, Mar. 16, 2011, pp. 4221-4232.
Chen et al., "Depression of motor cortex excitability by low-frequency transcranial magnetic stimulation," Neurology, vol. 48, No. 5, May 1997, pp. 1398-1403.
Chen et al., "Mechanisms of Cortical Reorganization in Lower-Limb Amputees," The Journal of Neuroscience, vol. 18, No. 9, May 1, 1998, pp. 3443-3450.
Cheng et al., "Different forms of prefrontal theta burst stimulation for executive function of medication- resistant depression: Evidence from a randomized sham-controlled study," Prog Neuropsychopharmacol Biol Psychiatry, vol. 66, 2016, pp. 35-40.
Chistyakov et al., "Safety, tolerability and preliminary evidence for antidepressant efficacy of theta-burst transcranial magnetic stimulation in patients with major depression.," International Journal of Neuropsychopharmacology, vol. 13, No. 3, Apr. 2010, Electronic Publication: Feb. 4, 2010, pp. 387-393.
Cho et al., "Continuous theta burst stimulation of right dorsolateral prefrontal cortex induces changes in impulsivity level," CIHR Author Manuscript, 16 p. Published in final form as: Brain Stimulation, vol. 3, No. 3, Jul. 2010, pp. 170-176.
Chung et al., "Impact of different intensities of intermittent theta burst stimulation on the cortical properties during TMS-EEG and working memory performance," Human Brain Mapping, vol. 39, No. 2, Feb. 2018, pp. 783-802.
Chung et al., "The effect of single and repeated prefrontal intermittent theta burst stimulation on cortical reactivity and working memory," Brain Stimulation, vol. 11, No. 3, May-Jun. 2018, pp. 566-574.
Chung et al., "The effects of individualised intermittent theta burst stimulation in the prefrontal cortex: A TMS-EEG study," Human Brain Mapping, vol. 40, No. 2, Feb. 1, 2019, pp. 608-627.
Cichon et al., "Branch-specific dendritic Ca2+ spikes cause persistent synaptic plasticity," Nature, vol. 520, No. 7546, Apr. 9, 2015, Electronic Publication: Mar. 30, 2015, pp. 180-185.
Ciobanu et al., "rTMS for pharmacoresistant major depression in the clinical setting of a psychiatric hospital: effectiveness and effects of age," Journal of Affective Disorders, vol. 150, No. 2, Sep. 5, 2013, pp. 677-681.
Cohen et al., "Effects of coil design on delivery of focal magnetic stimulation. Technical considerations," Electroencephalography and Clinical Neurophysiology, vol. 75, No. 4, Apr. 1990, pp. 350-357.
Daskalakis et al., "Repetitive transcranial magnetic stimulation for major depressive disorder: a review.," The Canadian Journal of Psychiatry, vol. 53, No. 9, Sep. 2008, pp. 555-566.
Defelipe, , "The evolution of the brain, the human nature of cortical circuits, and intellectual creativity," Frontiers in Neuroanatomy, vol. 5, No. 29, May 16, 2011, 17 Pgs.
Desmyter et al., "Accelerated Intermittent Theta Burst Stimulation for Suicide Risk in Therapy-Resistant Depressed Patients: A Randomized, Sham- Controlled Trial," Frontiers in Human Neuroscience, vol. 10, No. 480, Sep. 27, 2016, 7 Pgs.
Desmyter et al., "The Acute Effects of Accelerated Repetitive Transcranial Magnetic Stimulation on Suicide Risk in Unipolar Depression: Preliminary Results," Psychiatria Danubina, vol. 26, Suppl. 1, Nov. 2014, pp. 48-52.
Diekhoff-Krebs et al., "Interindividual differences in motor network connectivity and behavioral response to iTBS in stroke patients," NeuroImage: Clinical, vol. 15, 2017, pp. 559-571.
Drysdale et al., "Resting-state connectivity biomarkers define neurophysiological subtypes of depression," Nat. Med., Author Manuscript, Oct. 2, 2017, 35 Pgs.
Drysdale et al., "Resting-state connectivity biomarkers define neurophysiological subtypes of depression," Nature Medicine, No. 23, 2017, pp. 28-38, Published online Dec. 5, 2016, printed Mar. 21, 2017 from http://www.nature.com/nm/journal/v23/n1/ full/nm.4246.html, 5 Pgs.
Dumas et al., "[Repetitive transcranial magnetic stimulation in major depression: response factor].," Encephale, vol. 38, No. 4, Sep. 2012, Electronic Publication: Oct. 11, 2011, pp. 360-368.
Dunlop et al., "Functional Connectivity of the Subcallosal Cingulate Cortex and Differential Outcomes to Treatment with Cognitive-Behavioral Therapy of Antidepressant Medication for Major Depressive Disorder," Am. J. Psychiatry, Jun. 1, 2017, vol. 174, No. 6, pp. 533-545.
Duprat et al., "Accelerated intermittent theta burst stimulation treatment in medication-resistant major depression: A fast road to remission?," Journal of Affective Disorders, vol. 200, Aug. 2016, Electronic Publication: Apr. 19, 2016, pp. 6-14.
Eldaief et al., "Transcranial magnetic stimulation in neurology: A review of established and prospective applications," Neurology: Clinical Practice, vol. 3, No. 6, Dec. 2013, pp. 519-526.
Eldaief et al., "Transcranial magnetic stimulation modulates the brain's intrinsic activity in a frequency-dependent manner," Proceedings of the National Academy of Sciences, vol. 108, No. 52, Dec. 27, 2011, pp. 21229-21234.
Evers et al., "The impact of transcranial magnetic stimulation on cognitive processing: an event-related potential study," NeuroReport, vol. 12, No. 13, Sep. 17, 2001, pp. 2915-2918.
Fekadu et al., "A Multidimensional Tool to Quantify Treatment Resistance in Depression: The Maudsley Staging Method," Journal of Clinical Psychiatry, vol. 70, No. 2, Jan. 27, 2009, pp. 177-184.
Fekadu et al., "The Maudsley Staging Method for Treatment-Resistant Depression: Prediction of Longer-Term Outcome and Persistence of Symptoms," Journal of Clinical Psychiatry, vol. 70, No. 7, Jul. 2009, Electronic Publication: May 19, 2009, pp. 952-957.
Ferbert et al., "Interhemispheric Inhibition of the Human Motor Cortex," Journal of Physiology, vol. 453, 1992, pp. 525-546.
Fitzgerald et al., "The effects of repetitive transcranial magnetic stimulation in the treatment of depression," Expert Review of Medical Devices, vol. 8, No. 1, Jan. 2011, pp. 85-95.
Fox, , "113. Brain Lesions Associated With Depression are Characterized by a Unique Pattern of Brain Connectivity," Biological Psychiatry, vol. 83, No. 9, Supplement, May 1, 2018, pp. S46-S47.
Fox, , "Mapping Symptoms to Brain Networks with the Human Connectome," The New England Journal of Medicine, vol. 379, No. 23, Dec. 6, 2018, pp. 2237-2245.
Fox et al., "Efficacy of Transcranial Magnetic Stimulation Targets for Depression Is Related to Intrinsic Functional Connectivity with the Subgenual Cingulate," Biol. Psychiatry, 2012, vol. 72, pp. 595-603.
Fox et al., "Measuring and manipulating brain connectivity with resting state functional connectivity magnetic resonance imaging (fcMRI) and transcranial magnetic stimulation (TMS)," NeuroImage, vol. 62, No. 4, Oct. 1, 2012, pp. 2232-2243.

(56) References Cited

OTHER PUBLICATIONS

Fox et al., "Resting-state networks link invasive and noninvasive brain stimulation across diverse psychiatric and neurological diseases," Proc Natl Acad Sci, vol. 111, No. 41, Oct. 2014, pp. E4367-E4375.
Fregni et al., "Predictors of antidepressant response in clinical trials of transcranial magnetic stimulation," International Journal of Neuropsychopharmacology, vol. 9, No. 6, Dec. 2006, Electronic Publication: Nov. 23, 2005, pp. 641-654.
Fregni et al., "Technology Insight: noninvasive brain stimulation in neurology-perspectives on the therapeutic potential of rTMS and tDCS," Nature Clinical Practice Neurology, vol. 3, No. 7, Jul. 2007, pp. 383-393.
Froc et al., "Long-Term Depression and Depotentiation in the Sensorimotor Cortex of the Freely Moving Rat," The Journal of Neuroscience, vol. 20, No. 1, Jan. 1, 2000, pp. 438-445.
Gamboa et al., "Simply longer is not better: reversal of theta burst after-effect with prolonged stimulation," Experimental Brain Research, vol. 204, No. 2, Jul. 2010, Electronic Publication: Jun. 22, 2010, pp. 181-187.
George et al., "A two-site pilot randomized 3 day trial of high dose left prefrontal repetitive transcranial magnetic stimulation (rTMS) for suicidal inpatients," Brain Stimul, vol. 7, No. 3, 2014, pp. 421-431.
George et al., "Daily Left Prefrontal Transcranial Magnetic Stimulation Therapy for Major Depressive Disorder: A Sham-Controlled Randomized Trial," Archives Of General Psychiatry, vol. 67, No. 5, May 2010, pp. 507-516.
George et al., "Daily repetitive transcranial magnetic stimulation (rTMS) improves mood in depression," An International Journal for the Rapid Communication of Research in Neuroscience, vol. 6, No. 14, Oct. 2, 1995, pp. 1853-1856.
George et al., "The expanding evidence base for rTMS treatment of depression," Current Opinion in Psychiatry, vol. 26, No. 1, Jan. 2013, pp. 13-18.
Giesel et al., "Improvement of auditory hallucinations and reduction of primary auditory area's activation following TMS," European Journal of Radiology, vol. 81, No. 6, Jun. 2012, pp. 1273-1275.
Goldsworthy et al., "A comparison of two different continuous theta burst stimulation paradigms applied to the human primary motor cortex," Clinical Neurophysiology, 123, 2012, pp. 2256-2263.
Goldsworthy et al., "Neuroplastic Modulation of Inhibitory Motor Cortical Networks by Spaced Theta Burst Stimulation Protocols," Brain Stimulation, vol. 6, No. 3, May 2013, pp. 340-345.
Goldsworthy et al., "Spaced Noninvasive Brain Stimulation: Prospects for Inducing Long-Lasting Human Cortical Plasticity," Neurorehabilitation and Neural Repair, vol. 29, No. 8, Dec. 11, 2014, pp. 714-721.
Goldsworthy et al., "The application of spaced theta burst protocols induces long-lasting neuroplastic changes in the human motor cortex," European Journal of Neuroscience, vol. 35, No. 1, Nov. 25, 2011, pp. 125-134.
Gratton et al., "The effect of theta-burst TMS on cognitive control networks measured with resting state fMRI," Frontiers in Systems Neuroscience, vol. 7, No. 124, Dec. 2013, 14 Pgs.
Greenberg et al., "The Economic Burden of Depression in the United States: How Did It Change Between 1990 and 2000?," Journal of Clinical Psychiatry, vol. 64, No. 12, Dec. 2003, pp. 1465-1475.
Hadland et al., "Interference with Performance of a Response Selection Task that has no Working Memory Component: An rTMS Comparison of the Dorsolateral Prefrontal and Medial Frontal Cortex," Journal of Cognitive Neuroscience, vol. 13, No. 8, Nov. 15, 2001, pp. 1097-1108.
Hadley et al., "Safety, tolerability, and effectiveness of high doses of adjunctive daily left prefrontal repetitive transcranial magnetic stimulation for treatment-resistant depression in a clinical setting," J Ect, vol. 27, No. 1, Mar. 2011, pp. 18-25.
Hamilton, , "Development of a rating scale for primary depressive illness," The British Journal of Social and Clinical Psychology, vol. 6, No. 4, Dec. 1967, pp. 278-296.
Hanajima et al., "Paired-pulse magnetic stimulation of the human motor cortex: differences among I waves," Journal of Physiology, vol. 509, No. 2, Jun. 1998, pp. 607-618.
Harris et al., "Dendritic Spines: Cellular Specializations Imparting Both Stability and Flexibility to Synaptic Function," Annual Review of Neuroscience, vol. 17, Mar. 1994, pp. 341-371.
Hausmann et al., "No benefit derived from repetitive transcranial magnetic stimulation in depression: a prospective, single centre, randomised, double blind, sham controlled "add on" trial," Journal of Neurology, Neurosurgery, and Psychiatry, vol. 75, No. 2, Feb. 2004, pp. 320-322.
Hawco et al., "Spread of activity following TMS is related to intrinsic resting connectivity to the salience network: A concurrent TMS-fMRI study," Cortex, vol. 108, Nov. 2018, pp. 160-172.
Herwig et al., "Antidepressant effects of augmentative transcranial magnetic stimulation: Randomised multicentre trial," British Journal of Psychiatry, vol. 191, Nov. 2007, pp. 441-448.
Herwig et al., "Transcranial Magnetic Stimulation in Therapy Studies: Examination of the Reliability of "Standard" Coil Positioning by Neuronavigation," Biological Psychiatry, vol. 50, No. 1, Jul. 1, 2001, pp. 58-61.
Hess et al., "Conditions for the induction of long-term potentiation in layer II/III horizontal connections of the rat motor cortex," Journal of Neurophysiology, vol. 75, No. 5, May 1996, pp. 1765-1778.
Hess et al., "Long-term potentiation and long-term depression of horizontal connections in rat motor cortex," Acta Neurobiologiae Experimentalis Journal, vol. 56, No. 1, 1996, pp. 397-405.
Heusler et al., "A repetitive intracortical microstimulation pattern induces long-lasting synaptic depression in brain slices of the rat primary somatosensory cortex," Experimental Brain Research, vol. 135, No. 3, Dec. 2000, pp. 300-310.
Heynen et al., "Long-Term Potentiation of Thalamocortical Transmission in the Adult Visual Cortex In Vivo," The Journal of Neuroscience, vol. 21, No. 24, Dec. 15, 2001, pp. 9801-9813.
Hirsch et al., "Use-dependent changes in synaptic efficacy in rat prefrontal neurons in vitro," Journal of Physiology, vol. 427, No. 1, Aug. 1, 1990, pp. 31-49.
Holtzheimer III et al., "Accelerated repetitive transcranial magnetic stimulation for treatment-resistant depression," Depression & Anxiety, vol. 27, No. 10, Oct. 2010, pp. 960-963.
Huang et al., "The effect of short-duration bursts of high-frequency, low- intensity transcranial magnetic stimulation on the human motor cortex," Clinical Neurophysiology, vol. 115, No. 5, May 2004, pp. 1069-1075.
Huang et al., "The theoretical model of theta burst form of repetitive transcranial magnetic stimulation," Clinical Neurophysiology, vol. 122, No. 5, May 2011, pp. 1011-1018.
Huang et al., "Theta Burst Stimulation of the Human Motor Cortex," Neuron, vol. 45, No. 2, Jan. 20, 2005, pp. 201-206.
Huemmeke et al., "Metabotropic glutamate receptors mediate expression of LTP in slices of rat visual cortex," European Journal of Neuroscience, vol. 15, No. 10, May 2002, pp. 1641-1645.
Hung et al., "Visual Selection and the Human Frontal Eye Fields: Effects of Frontal Transcranial Magnetic Stimulation on Partial Report Analyzed by Bundesen's Theory of Visual Attention," The Journal of Neuroscience, vol. 31, No. 44, Nov. 2, 2011, pp. 15904-15913.
Jiang et al., "The organization of two new cortical interneuronal circuits," Nature Neuroscience, vol. 16, No. 2, Feb. 2013, Electronic Publication: Jan. 13, 2013, pp. 210-218.
Juan et al., "Feedback to V1: a reverse hierarchy in vision," Experimental Brain Research, vol. 150, No. 2, Apr. 8, 2003, pp. 259-263.
Kadvany, , "Through Stanford brain research, the depressed feel 'whole' again," Palo Alto Online, Oct. 27, 2017, retrieved from: https://paloaltoonline.com/news/print/2017/10/27/becomingwholeagain on Jan. 8, 2018, 5 Pgs.

(56) References Cited

OTHER PUBLICATIONS

Kammer et al., "Transcranial magnetic stimulation in the visual system. I. The psychophysics of visual suppression," Experimental Brain Research, vol. 160, No. 1, Jan. 2005, pp. 118-128.
Kim et al., "Inhibitory control of excitable dendrites in neocortex," Journal of Neurophysiology, vol. 74, No. 4, Oct. 1995, pp. 1810-1814.
Kimbrell et al., "Regional Cerebral Glucose Utilization in Patients with a Range of Severities of Unipolar Depression," Biological Psychiatry, vol. 51, No. 3, Feb. 1, 2002, pp. 237-252.
Kobayashi et al., "Ipsilateral motor cortex activation on functional magnetic resonance imaging during unilateral hand movements is related to interhemispheric interactions," NeuroImage, vol. 20, No. 4, Dec. 2003, pp. 2259-2270.
Kozel et al., "How Coil-Cortex Distance Relates to Age, Motor Threshold, and Antidepressant Response to Repetitive Transcranial Magnetic Stimulation," Journal of Neuropsychiatry and Clinical Neurosciences, vol. 12, No. 3, Aug. 2000, pp. 376-384.
Kramar et al., "Synaptic evidence for the efficacy of spaced learning," Proceedings of the National Academy of Sciences, vol. 109, No. 13, Mar. 27, 2012, pp. 5121-5126.
Kujirai et al., "Corticocortical inhibition in human motor cortex," Journal of Physiology, vol. 471, No. 1, Nov. 1, 1993, pp. 501-519.
Larkum, , "A cellular mechanism for cortical associations: an organizing principle for the cerebral cortex," Trends in Neurosciences, vol. 36, No. 3, Mar. 2013, pp. 141-151.
Larkum et al., "A new cellular mechanism for coupling inputs arriving at different cortical layers," Nature, vol. 398, Mar. 25, 1999, pp. 338-341.
Larkum et al., "Synaptic Integration in Tuft Dendrites of Layer 5 Pyramidal Neurons: A New Unifying Principle," Science, vol. 325, No. 5941, Aug. 7, 2009, pp. 756-760.
Larson et al., "Induction of Synaptic Potentiation in Hippocampus by Patterned Stimulation Involves Two Events," Science, vol. 232, No. 4753, May 23, 1986, pp. 985-988.
Lavzin et al., "Nonlinear dendritic processing determines angular tuning of barrel cortex neurons in vivo," Nature, vol. 490, Oct. 18, 2012, pp. 397-401.
Lee et al., "Acute Remapping within the Motor System Induced by Low- Frequency Repetitive Transcranial Magnetic Stimulation," The Journal of Neuroscience, vol. 23, No. 12, Jun. 15, 2003, pp. 5308-5318.
Lee et al., "Canonical Organization of Layer 1 Neuron-Led Cortical Inhibitory and Disinhibitory Interneuronal Circuits," Cerebral Cortex, vol. 25, No. 8, Aug. 2015, Electronic Publication: Feb. 18, 2014, pp. 2114-2126.
Lee et al., "The effects of inhibitory and facilitatory intracortical circuits on interhemispheric inhibition in the human motor cortex," The Journal of Physiology, vol. 580, Pt. 3, May 1, 2007, Published Online: Feb. 15, 2007, pp. 1021-1032.
Lehrer et al., "Heart rate variability biofeedback: how and why does it work?," Frontiers in Psychology, vol. 5, No. 756, Jul. 21, 2014, pp. 1-9.
Lemogne et al., "Self-referential processing and the prefrontal cortex over the course of depression: A pilot study," Journal of Affective Disorders, vol. 124, No. 1-2, Jul. 2010, pp. 196-201.
Levinson et al., "Evidence of Cortical Inhibitory Deficits in Major Depressive Disorder," Biological Psychiatry, vol. 67, No. 5, Mar. 1, 2010, pp. 458-464.
Li et al., "Antidepressant mechanism of add-on repetitive transcranial magnetic stimulation in medication-resistant depression using cerebral glucose metabolism," Journal of Affective Disorders, vol. 127, No. 1-3, Dec. 2010, pp. 219-229.
Li et al., "Efficacy of prefrontal theta-burst stimulation in refractory depression: a randomized sham-controlled study," Brain: A Journal of Neurology, vol. 137, May 10, 2014, pp. 2088-2098.
Li et al., "Impaired Prefronto-Thalamic Functional Connectivity as a Key Feature of Treatment-Resistant Depression: A Combined Meg, Pet and rTMS Study," Plos One, vol. 8, No. 8, Aug. 2, 2013, 8 Pgs.
Li et al., "Major Depressive Disorder and Stroke Risks: A 9-Year Follow-Up Population-Based, Matched Cohort Study," Plos One, vol. 7, No. 10, Oct. 8, 2012, 9 Pgs.
Li et al., "Structural and cognitive deficits in remitting and non-remitting recurrent depression: A voxel-based morphometric study," NeuroImage, vol. 50, No. 1, Mar. 2010, pp. 347-356.
Lisanby et al., "Daily Left Prefrontal Repetitive Transcranial Magnetic Stimulation in the Acute Treatment of Major Depression: Clinical Predictors of Outcome in a Multisite, Randomized Controlled Clinical Trial," Neuropsychopharmacology, vol. 34, No. 2, Jan. 2009, Electronic Publication: Aug. 13, 2008, pp. 522-534.
Liu et al., "Role of NMDA Receptor Subtypes in Governing the Direction of Hippocampal Synaptic Plasticity," Science, vol. 304, No. 5673, May 14, 2004, pp. 1021-1024.
Losonczy et al., "Integrative Properties of Radial Oblique Dendrites in Hippocampal CA1 Pyramidal Neurons," Neuron, vol. 50, No. 2, Apr. 20, 2006, pp. 291-307.
Lovett-Barron et al., "Behavioral consequences of GABAergic neuronal diversity," Current Opinion in Neurobiology, vol. 26, Jun. 2014, pp. 27-33.
Lynch et al., "Differences Between Synaptic Plasticity Thresholds Result in New Timing Rules for Maximizing Long-Term Potentiation," Neuropharmacology, vol. 61, No. 1, Jan. 2013, pp. 27-36.
Maeda et al., "Interindividual variability of the modulatory effects of repetitive transcranial magnetic stimulation on cortical excitability," Experimental Brain Research, vol. 133, No. 4, Aug. 2000, pp. 425-430.
Martin et al., "Repetitive transcranial magnetic stimulation for the treatment of depression: Systematic review and meta-analysis," British Journal of Psychiatry, vol. 182, Jun. 2003, pp. 480-491.
McDonald et al., "Improving the antidepressant efficacy of transcranial magnetic stimulation: Maximizing the number of stimulation and treatment location in treatment resistant depression," Depression & Anxiety, vol. 28, No. 11, Nov. 2011, published online Sep. 2, 2011, pp. 973-980.
Modirrousta et al., "Efficacy of twice-daily vs once-daily sessions of repetitive transcranial magnetic stimulation in the treatment of major depressive disorder: a retrospective study," Neuropsychiatric Disease and Treatment, vol. 14, Dec. 7, 2017, pp. 309-316.
Muellbacher et al., "Effects of low-frequency transcranial magnetic stimulation on motor excitability and basic motor behavior," Clinical Neurophysiology, vol. 111, No. 6, Jun. 1, 2000, pp. 1002-1007.
Mueller et al., "Simultaneous transcranial magnetic stimulation and single- neuron recording in alert non-human primates," Nature Neuroscience, vol. 17, No. 8, Aug. 2014, Electronic Publication: Jun. 29, 2014, pp. 1130-1136.
Murayama et al., "Dendritic encoding of sensory stimuli controlled by deep cortical interneurons," Nature, vol. 457, No. 7233, Feb. 26, 2009, Electronic Publication: Jan. 18, 2009, pp. 1137-1141.
Murayama et al., "Fiberoptic System for Recording Dendritic Calcium Signals in Layer 5 Neocortical Pyramidal Cells in Freely Moving Rats," Journal of Neurophysiology, vol. 98, No. 3, Sep. 2007, pp. 1791-1805.
Murd et al., "Repetitive TMS over V5/MT shortens the duration of spatially localized motion aftereffect: The effects of pulse intensity and stimulation hemisphere," Vision Research, vol. 68, Sep. 1, 2012, pp. 59-64.
Murphy et al., "Transcranial magnetic stimulation (TMS) inhibits cortical dendrites," ELife, vol. 5, Mar. 18, 2016, 12 Pgs.
Nettekoven et al., "Dose-Dependent Effects of Theta Burst rTMS on Cortical Excitability and Resting-State Connectivity of the Human Motor System," Journal of Neuroscience, vol. 34, No. 20, May 14, 2014, pp. 6849-6859.
Nettekoven et al., "Inter-individual variability in cortical excitability and motor network connectivity following multiple blocks of rTMS," NeuroImage, vol. 118, Sep. 2015, Electronic Publication: Jun. 5, 2015, pp. 209-218.
Nishiyama et al., "Calcium stores regulate the polarity and input specificity of synaptic modification," Nature, vol. 408, No. 6812, Nov. 30, 2000, pp. 584-588.
Nitsche et al., "Excitability changes induced in the human motor cortex by weak transcranial direct current stimulation," Journal of Physiology, vol. 527, Pt. 3, Sep. 15, 2000, pp. 633-639.

(56) References Cited

OTHER PUBLICATIONS

Nyffeler et al., "Extending lifetime of plastic changes in the human brain," European Journal of Neuroscience, vol. 24, No. 10, Nov. 2006, pp. 2961-2966.
Nyffeler et al., "One Session of Repeated Parietal Theta Burst Stimulation Trains Induces Long-Lasting Improvement of Visual Neglect," Stroke, vol. 40, No. 8, Jun. 11, 2009, pp. 2791-2796.
Oathes et al., "Individualized non-invasive brain stimulation engages the subgenual anterior cingulate and amygdala," bioRxiv, Dec. 21, 2018, 35 Pgs.
Ogiue-Ikeda et al., "The effect of repetitive transcranial magnetic stimulation on long-term potentiation in rat hippocampus depends on stimulus intensity," Brain Research, vol. 993, No. 1-2, Dec. 12, 2003, pp. 222-226.
Olah et al., "Output of neurogliaform cells to various neuron types in the human and rat cerebral cortex," Frontiers in Neural Circuits, vol. 1, No. 4, Nov. 2007, 7 Pgs.
Olah et al., "Regulation of cortical microcircuits by unitary GABA-mediated vol. transmission," Nature, vol. 461, No. 7268, Oct. 29, 2009, pp. 1278-1281.
O'Reardon et al., "Efficacy and Safety of Transcranial Magnetic Stimulation in the Acute Treatment of Major Depression: A Multisite Randomized Controlled Trial," Biological Psychiatry, vol. 62, No. 11, Dec. 1, 2007, pp. 1208-1216.
Palmer et al., "Inhibitory regulation of dendritic activity in vivo," Frontiers in Neural Circuits, vol. 6, No. 26, May 2012, 10 Pgs.
Palmer et al., "The Cellular Basis of GABAB-Mediated Interhemispheric Inhibition," Science, vol. 335, No. 6071, Feb. 24, 2012, pp. 989-993.
Pascual-Leone et al., "Fast Backprojections from the Motion to the Primary Visual Area Necessary for Visual Awareness," Science, vol. 292, No. 5516, Apr. 20, 2001, pp. 510-512.
Pashut et al., "Mechanisms of Magnetic Stimulation of Central Nervous System Neurons," PLOS Computational Biology, vol. 7, No. 3, Mar. 24, 2011, 18 Pgs.
Pashut et al., "Patch-clamp recordings of rat neurons from acute brain slices of the somatosensory cortex during magnetic stimulation," Frontiers in Cellular Neuroscience, vol. 8, No. 145, Jun. 2014, 12 Pgs.
Peinemann et al., "Long-lasting increase in corticospinal excitability after 1800 pulses of subthreshold 5 Hz repetitive TMS to the primary motor cortex," Clinical Neurophysiology, vol. 115, No. 7, Jul. 2004, pp. 1519-1526.
Perellon-Alfonso et al., "Similar effect of intermittent theta burst and sham stimulation on corticospinal excitability: A 5-day repeated sessions study," European Journal of Neuroscience, vol. 48, No. 4, Aug. 2018, pp. 1990-2000.
Perez-Garci et al., "Inhibition of dendritic Ca2+ spikes by GABAB receptors in cortical pyramidal neurons is mediated by a direct Gi/o-By-subunit interaction with Cav1 channels," Journal of Physiology, vol. 591, No. 7, Apr. 2013, pp. 1599-1612.
Perez-Garci et al., "The GABAB1b Isoform Mediates Long-Lasting Inhibition of Dendritic Ca2+ Spikes in Layer 5 Somatosensory Pyramidal Neurons," Neuron, vol. 50, May 18, 2006, pp. 603-616.
Plewnia et al., "Treatment of major depression with bilateral theta burst stimulation: A randomized controlled pilot trial," Journal of Affective Disorders, vol. 156, Mar. 1, 2014, pp. 219-223.
Polsky et al., "Computational subunits in thin dendrites of pyramidal cells," Nature Neuroscience, vol. 7, No. 6, May 23, 2004, pp. 621-627.
Reis et al., "Topiramate Selectively Decreases Intracortical Excitability in Human Motor Cortex," Epilepsia, vol. 43, No. 10, Oct. 2002, pp. 1149-1156.
Ridding et al., "Changes in motor cortical excitability induced by paired associative stimulation," Clinical Neurophysiology, vol. 114, No. 8, Aug. 2003, pp. 1437-1444.
Rossi et al., "Safety, ethical considerations, and application guidelines for the use of transcranial magnetic stimulation in clinical practice and research," Clinical Neurophysiology, vol. 120, No. 12, Dec. 2009, pp. 2008-2039.
Ruchsow et al., "Electrophysiological evidence for reduced inhibitory control in depressed patients in partial remission: A Go/Nogo study," International Journal of Psychophysiology, vol. 68, No. 3, Jun. 2008, pp. 209-218.
Ruhe et al., "Staging methods for treatment resistant depression. A systematic review.," Journal of Affective Disorders, vol. 137, No. 1-3, Mar. 2012, pp. 35-45.
Rush, , "Limitations in Efficacy of Antidepressant Monotherapy," Journal of Clinical Psychiatry, vol. 68, Suppl. 10, 2007, pp. 8-10.
Samson et al., "Brain activation predicts treatment improvement in patients with major depressive disorder," Journal of Psychiatric Research, vol. 45, No. 9, Sep. 2011, pp. 1214-1222.
Shen et al., "Synaptic Plasticity in Rat Subthalamic Nucleus Induced by High- Frequency Stimulation," Synapse, vol. 50, No. 4, Dec. 15, 2003, pp. 314-319.
Shimojo et al., "What visual perception tells US about mind and brain," Proceedings of the National Academy of Sciences, vol. 98, No. 22, Oct. 23, 2001, pp. 12340-12341.
Sibille et al., "GABA-related transcripts in the dorsolateral prefrontal cortex in mood disorders," International Journal of Neuropsychopharmacology, vol. 14, No. 6, Jul. 2011, pp. 721-734.
Siebner et al., "How does transcranial magnetic stimulation modify neuronal activity in the brain? Implications for studies of cognition," Cortex, vol. 45, No. 9, Oct. 2009, pp. 1035-1042.
Siebner et al., "Lasting cortical activation after repetitive TMS of the motor cortex: A glucose metabolic study," Neurology, vol. 54, No. 4, Feb. 22, 2000, pp. 956-963.
Siebner et al., "Patients with focal arm dystonia have increased sensitivity to slow-frequency repetitive TMS of the dorsal premotor cortex," Brain, vol. 126, No. 12, Dec. 1, 2003, pp. 2710-2725.
Silvanto et al., "Striate cortex (V1) activity gates awareness of motion," Nature Neuroscience, vol. 8, No. 2, Feb. 2005, pp. 143-144.
Smith et al., "Dendritic spikes enhance stimulus selectivity in cortical neurons in vivo," Nature, vol. 503, Nov. 7, 2013, pp. 115-120.
Smolen et al., "The right time to learn: mechanisms and optimization of spaced learning," Nature Reviews Neuroscience, vol. 17, Feb. 2016, pp. 77-88.
Sparing et al., "Repetitive Transcranial Magnetic Stimulation Effects on Language Function Depend on the Stimulation Parameters," Journal of Clinical Neurophysiology, vol. 18, No. 4, Jul. 2001, pp. 326-330.
Spronk et al., "Long Term Effects of Left Frontal rTMS on EEG and ERPs in Patients with Depression," Clinical EEG and Neuroscience, vol. 39, No. 3, Jul. 2008, pp. 118-124.
Stefan et al., "Induction of plasticity in the human motor cortex by paired associative stimulation," Brain, vol. 123, No. 3, Mar. 1, 2000, pp. 572-584.
Stokes et al., "Simple Metric For Scaling Motor Threshold Based on Scalp- Cortex Distance: Application to Studies Using Transcranial Magnetic Stimulation," J Neurophysiol, 94, 2005, pp. 4520-4527.
Suppa et al., "Theta burst stimulation induces after-effects on contralateral primary motor cortex excitability in humans," The Journal of Physiology, vol. 586, No. 18, Sep. 2008, pp. 4489-4500.
Takita et al., "Induction of stable long-termdepression in vivo in the hippocampal prefrontal cortex pathway," European Journal of Neuroscience, vol. 11, No. 11, Nov. 1999, pp. 4145-4148.
Tamas et al., "Identified Sources and Targets of Slow Inhibition in the Neocortex," Science, vol. 299, No. 5614, Mar. 21, 2003, pp. 1902-1905.
Terao et al., "Basic mechanisms of TMS," Journal of Clinical Neurophysiology, vol. 19, No. 4, Aug. 2002, pp. 322-343.
Trepel et al., "Long-term Potentiation in the Neocortex of the Adult, Freely Moving Rat," Cerebral Cortex, vol. 8, No. 8, Dec. 1998, pp. 719-729.
Vickery et al., "Metabotropic Glutamate Receptors Are Involved in Long-Term Potentiation in Isolated Slices of Rat Medial Frontal Cortex," Journal of Neurophysiology, vol. 78, No. 6, Dec. 1997, pp. 3039-3046.
Vink et al., "A novel concurrent TMS-fMRI method to reveal propagation patterns of prefrontal magnetic brain stimulation," Human Brain Mapping, vol. 39, No. 11, Nov. 2018, pp. 4580-4592.

(56) References Cited

OTHER PUBLICATIONS

Wagner et al., "Transcranial magnetic stimulation and stroke: A computer-based human model study," NeuroImage, vol. 30, No. 3, Apr. 15, 2006, pp. 857-870.
Wassermann, , "Risk and safety of repetitive transcranial magnetic stimulation: report and suggested guidelines from the International Workshop on the Safety of Repetitive Transcranial Magnetic Stimulation," Electroencephalography and Clinical Neurophysiology, vol. 108, 1998, pp. 1-16.
Weigand et al., "Prospective Validation That Subgenual Connectivity Predicts Antidepressant Efficacy of Transcranial Magnetic Stimulation Sites," Biological Psychiatry, vol. 84, No. 1, Jul. 1, 2018, pp. 28-37.
Williams et al., "Five-Year Follow-Up of Bilateral Epidural Prefrontal Cortical Stimulation for Treatment-Resistant Depression," Brain Stimul, 9, 2016, pp. 897-904.
Williams et al., "High-dose spaced theta-burst TMS as a rapid-acting antidepressant in highly refractory despression," Brain, vol. 141, No. 3, Mar. 2018.
Williams et al., "Optimization of epidural cortical stimulation for treatment-resistant depression," Brain Stimulation, vol. 11, No. 1, Jan.-Feb. 2018, pp. 239-240.
Wozny et al., "Specificity of Synaptic Connectivity between Layer 1 Inhibitory Interneurons and Layer 2/3 Pyramidal Neurons in the Rat Neocortex," Cerebral Cortex, vol. 21, No. 8, Aug. 1, 2011, pp. 1818-1826.
Wu et al., "Theta-Burst Repetitive Transcranial Magnetic Stimulation For Treatment-Resistant Obsessive-Compulsive Disorder With Concomitant Depression," The Journal of Clinical Psychiatry, vol. 71, No. 4, Apr. 2010, pp. 504-506.
Xu et al., "Nonlinear dendritic integration of sensory and motor input during an active sensing task," Nature, vol. 492, Dec. 13, 2012, pp. 247-251.
Yip et al., "61% of unmedicated treatment resistant depression patients who did No. respond to acute TMS treatment responded after four weeks of twice weekly deep TMS in the Brainsway pivotal trial," Brain stimul, 10, 2017, pp. 847-849.
Zanto et al., "Causal role of the prefrontal cortex in top-down modulation of visual processing and working memory," Nature Neuroscience, vol. 14, No. 5, May 2011, pp. 656-661.
Ziemann, , "TMS in cognitive neuroscience: Virtual lesion and beyond," Cortex, vol. 46, No. 1, Jan. 2010, pp. 124-127.
Ziemann et al., "Modulation of Plasticity in Human Motor Cortex after Forearm Ischemic Nerve Block," The Journal of Neuroscience, vol. 18, No. 3, Feb. 1, 1998, pp. 1115-1123.
Chen et al., "Left Versus Right Repetitive Transcranial Magnetic Stimulation in Treating Major Depression: A Meta-Analysis of Randomised Controlled Trials", Elsevier, Psychiatry Research, 2013, 210, pp. 1260-1264.
Extended European Search Report for European Application No. 19738551.1, Search completed Aug. 16, 2021, Mailed Aug. 25, 2021, 13 Pgs.
Baeken et al., "Intensive HF-rTMS treatment in refractory medication-resistant unipolar depressed patients", Journal of Affective Disorders, Available online Jul. 26, 2013, vol. 151, No. 2, pp. 625-631.
Downar, "Optimizing the Inter-Session Interval for Accelerated rTMS", Brain Stimulation, Mar. 2017, vol. 10, Issue No. 2, pp. 456-457, Doi: 10.1016/J.BRS.2017.01.340.
Gamboa et al., "Impact of repetitive theta burst stimulation on motor cortex excitability", Brain Stimulation, vol. 4, No. 3, Jul. 2011, pp. 141-151, doi: https://doi.org/10.1016/j.brs.2010.09.008.
Klomjai et al., "Basic Principles of Transcranial Magnetic Stimulation (TMS) and Repetitive TMS (rTMS)", Annals of Physical and Rehabilitation Medicine, Sep. 1, 2015, vol. 58, Issue No. 4, p. 208-213.
Sonmez et al., "Accelerated TMS for Depression: A systematic review and meta-analysis", Psychiatry Res., Mar. 2019, vol. 273, pp. 770-781, doi: 10.1016/j.psychres.2018.12.041.
Williams, "Accelerated rTMS: Pragmatic Considerations for the Development of an Inpatient rTMS Approach", Brain Stimulation, Mar. 2017, vol. 10, Issue No. 2, DOI: 10.1016/J.BRS.2017.01.269, p. 427.
Extended European Search Report for European Application No. 25169210.9, Search completed Oct. 15, 2025, Mailed Oct. 31, 2025, 11 Pgs.
Iseger et al., "Neuro-Cardiac-Guided Tms (NCG-TMS): Probing DLPFC-sgACC-vagus nerve connectivity using heart rate—First results", Brain Stimulation, vol. 10, No. 5, 2017, pp. 1006-1008.
Liston, Conor, "fMRI-guided methods for rTMS targeting and treatment prediction", Brain Stimulation, vol. 14, No. 6, Nov. Dec. 2021.

* cited by examiner

| Day 1 | Day 2 | Day 3 | Day 4 | Day 5 |
|---|---|---|---|---|
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |
| 50 min ISI | 50 min ISI | 50 min ISI | 50 min ISI | 50 min ISI |
| iTBS1800 | iTBS1800 | iTBS1800 | iTBS1800 | iTBS1800 |

*FIG. 4*

FIG. 5

| Day 1 | Day 2 | Day 3 | Day 4 | Day 5 |
|---|---|---|---|---|
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |
| 15 min ISI | 15 min ISI | 15 min ISI | 15 min ISI | 15 min ISI |
| cTBS600 | cTBS600 | cTBS600 | cTBS600 | cTBS600 |

SYSTEMS AND METHODS FOR PERSONALIZED TREATMENT OF NEUROLOGICAL CONDITIONS USING IMPLANTABLE NEUROSTIMULATORS

CROSS REFERENCE TO RELATED APPLICATIONS

The present invention is a continuation application of U.S. patent application Ser. No. 16/215,519 entitled "Systems and Methods for Personalized Treatment of Neurological Conditions using Implantable Neurostimulators" filed Dec. 10, 2018, which claims priority to U.S. Provisional Patent Application Ser. No. 62/617,121 entitled "Systems and Methods for Personalized Clinical Applications of Accelerated Theta-Burst Stimulation" filed Jan. 12, 2018. U.S. Provisional Patent Application Ser. No. 62/617,121 and U.S. patent application Ser. No. 16/215,519 are incorporated by reference in their entirety herein.

FIELD OF THE INVENTION

The present invention generally relates to personalized treatment of neurological conditions, namely depression, among others, using implantable neurostimulators.

BACKGROUND

Transcranial Magnetic Stimulation (TMS) is a non-invasive medical procedure where strong magnetic fields are utilized to stimulate specific areas of a patient's brain in order to treat a medical condition such as depression and neuropathic pain. Repeated applications of TMS in a short time frame is referred to as repetitive TMS (rTMS). Theta-burst stimulation (TBS) is a patterned form of rTMS, typically administered as a triplet of stimuli with 20 ms between each stimuli in the triplet, the triplet being repeated every 200 ms When TBS is performed continuously, this results in inhibition and is termed continuous theta burst stimulation (cTBS), and when done intermittently with inter-train intervals between the triplets, this is excitatory and termed intermittent theta-burst stimulation (iTBS).

Functional Magnetic Resonance Imaging (fMRI) is a non-invasive imaging technique where neuronal activity is measured by tracking hemodynamic responses in the brain. The resting state of a brain is the measurement of neuronal activity when the patient is not performing an explicit task. The resting state of a brain can be used to explore the connectivity between various structures and regions in the brain. A common example of a resting state connectivity is the default mode network (DMN). A particular resting state connectivity between brain regions that share functional properties is called a Resting State Functional Connectivity (RSFC).

SUMMARY OF THE INVENTION

Systems and methods for treatment of neurological conditions using implantable neurostimulators in accordance with embodiments of the invention are illustrated. One embodiment includes a method for treating neurological conditions, including obtaining functional magnetic resonance imaging (fMRI) image data of a patient's brain, where the fMRI image data describes neuronal activations within the patient's brain, determining a location on the patient's brain to implant a neurostimulator by, mapping at least one region of interest to the patient's brain, locating functional subregions within the at least one region of interest based on the fMRI image data, determining functional relationships between at least two functional subregions, generating subregion parameters for each functional subregion, generating a target quality score for each functional subregion based on the subregion parameters, and selecting a location for implanting the neurostimulator based on its target quality score and a patient's neurological condition, surgically implanting a neurostimulator at the location, and applying a stimulation protocol to the brain at the location using the neurostimulator to treat the neurological condition.

In another embodiment, the fMRI image data describes neuronal activity during a resting state.

In a further embodiment, obtaining the fMRI image data further includes preprocessing the fMRI image data.

In still another embodiment, preprocessing the fMRI image data includes performing at least one preprocessing step selected from the group consisting of physiological noise regression, slice-time correction, motion correction, co-registration, band-pass filtering, and de-trending.

In a still further embodiment, a brain atlas is used for mapping the at least one subregion.

In yet another embodiment, the each functional subregion describes homogenous brain activity.

In a yet further embodiment, functional subregions are located using hierarchical agglomerative clustering.

In another additional embodiment, subregion parameters are selected from the group consisting of size of the functional subregion, concentration of voxels that make up the functional subregion, the correlation between the functional subregion and other functional subregions, and accessibility of the subregion from the surface of the brain.

In a further additional embodiment, the target quality score reflects the surface influence for a given subregion.

In another embodiment again, the surface influence for a given subregion is the sum of a two dimensional matrix of Spearman correlation coefficients derived from a hierarchical clustering algorithm describing the correlation coefficients between a subregion on the surface of the brain and all subregions located deep within the brain.

In a further embodiment again, the aTBS protocol is an aiTBS protocol.

In still yet another embodiment, the aiTBS protocol includes applying a set of pulse trains, where each pulse train includes a set of pulses between 20 Hz and 70 Hz, applied at between 3 Hz to 7 Hz.

In a still yet further embodiment, the aiTBS protocol further includes applying the set of pulse trains between every 4 to 10 seconds for at least one 10 minute session.

In still another additional embodiment, the aiTBS protocol further includes conducting between 3 and 15 sessions per day, with between 25 and 120 minutes between each session.

In a still further additional embodiment, the aiTBS protocol includes applying a set of 2 second pulse trains, where each train includes magnetic stimulation pulses in the form of three 50 Hz pulses at 5 Hz, where the 2 second trains are applied every 10 seconds for at least ten 10 minute sessions, with an intersession interval of 50 minutes.

In still another embodiment again, the aTBS protocol is an acTBS protocol.

In a still further embodiment again, the acTBS protocol includes applying a set of pulse trains, where each pulse is between 20 Hz to 70 Hz, and each pulse is applied at between 3 Hz to 7 Hz, where each pulse train is applied between every 4 to 10 seconds for at least one session lasting between 40 and 44 seconds.

In yet another additional embodiment, the acTBS protocol further includes applying between 10 and 40 sessions per day.

In a yet further additional embodiment, the intersession interval is between 10 and 50 minutes.

In yet another embodiment again, the acTBS protocol includes a set of 3-pulse trains, where each pulse is 50 Hz applied at 5 Hz for at least one 40 second session.

In a yet further embodiment again, the acTBS protocol includes a set of 3-pulse trains, where each pulse is 30 Hz applied at 6 Hz for at least one 44 second session. In another additional embodiment again, the aTBS protocol is applied over at least 2 consecutive days.

In a further additional embodiment again, the neurological condition is clinical depression.

In still yet another additional embodiment, the neurological condition is suicidal ideation.

In another embodiment, an implantable neurostimulator is configured to apply an aTBS protocol to a patient's brain.

In a further embodiment, the aTBS protocol is an aiTBS protocol.

In still another embodiment, the aTBS protocol is an acTBS protocol.

In a still further embodiment, the implantable neurostimulator is further configured to intermittently apply the aTBS protocol.

In yet another embodiment, the implantable neurostimulator is further configured to continuously apply the aTBS protocol.

In a yet further embodiment, the implantable neurostimulator is further configured to apply the aTBS protocol at a regular interval.

In another additional embodiment, the implantable neurostimulator is further configured to apply the aTBS protocol based on patient feedback.

In a further additional embodiment, the parameters of the aTBS protocol are changed in response to the patient feedback.

In another embodiment again, the patient feedback is the patient's brain activity.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 4 is a stimulation schedule for accelerated intermittent Theta-Burst Stimulation in accordance with an embodiment of the invention.

FIG. 5 is a stimulation schedule for accelerated continuous Theta-Burst Stimulation in accordance with an embodiment of the invention.

DETAILED DESCRIPTION

Figure 1:
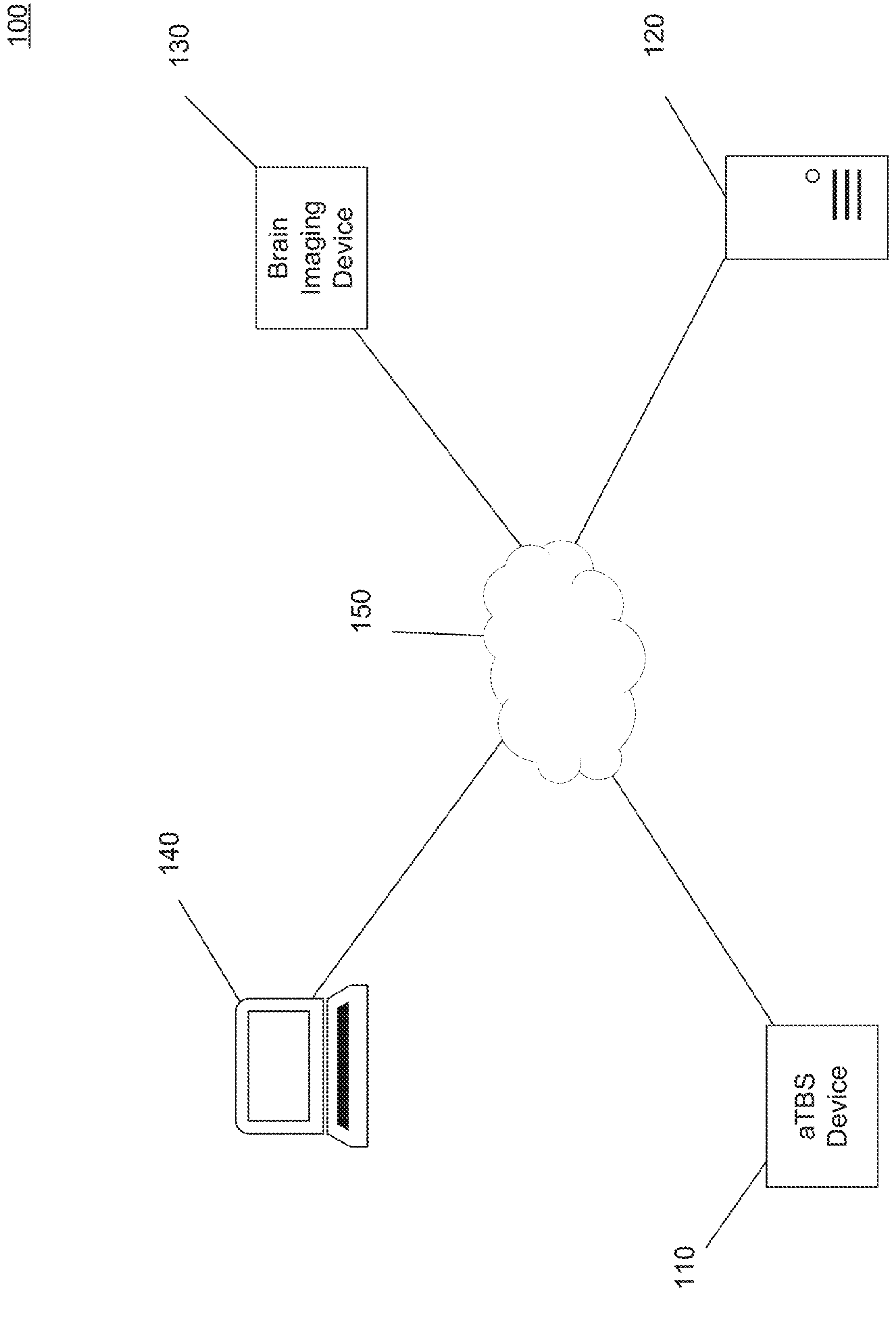
FIG. 1 is a diagram illustrating an accelerated Theta-Burst Stimulation system in accordance with an embodiment of the invention.

Brain stimulation has been used in several forms to treat mental health conditions. For example, techniques such as, but not limited to, vagus nerve stimulation, TMS, magnetic seizure therapy, and deep brain stimulation can be used as potential treatments for various mental health conditions, including depression, with varying efficacy. While non-invasive treatments such as TMS are often preferable for patients, there are many situations in which invasive measures are viable options for treatment. For example, long term stimulation can be achieved using implantable neurostimulators which can prevent a patient from being bound to hospitals for continuous treatment. Further, patients who are not responding optimally to non-invasive methods may respond better to invasive methods of stimulation. Indeed, there are any number of reasons why a medical professional may recommend invasive stimulation methods. While the below discusses brain stimulation with respect to specialized forms of rTMS, similar brain stimulation schemes can be applied using implantable neurostimulators. Implantable neurostimulators can provide stimulation using any number of stimulation methods, including, but not limited to, magnetic stimulation and/or electrical stimulation.

Turning now to the drawings, systems and methods for personalized clinical applications of accelerated intermittent theta-burst magnetic stimulation in accordance with embodiments of the invention are illustrated. rTMS has been accepted as an effective treatment for clinical depression by the U.S. Food and Drug Administration for nearly a decade and single daily application of iTBS (3 min, 600 pulses) has been approved by the FDA recently. Recently, a new form of rTMS known as Theta-Burst Stimulation has been shown in its (excitatory) intermittent form (iTBS) to have an increase in efficiency over standard rTMS by reducing the amount of time the treatment needs to be applied to have a therapeutic effect. For example, 40 minutes of TMS (approximately 3000 pulses) has been shown to be non-inferior to 3 minutes of iTBS (approximately 600 pulses). However, conventional rTMS/TBS treatment regimens can take multiple weeks of sessions to achieve a stable and effective reduction in clinical symptoms. Further, conventional rTMS and iTBS techniques have targeted portions of the brain based on averages of total activity within a region. Such techniques have failed to generate targets optimized for a patient's individualized brain structure and connectivity.

Accelerated Theta-Burst Stimulation (aTBS) is a new class of rTMS variants described herein in which large quantities of TBS pulses are applied over a short period to a targeted location within the brain. This can be accomplished to produce excitation (intermittent) or to produce inhibition (continuous). Appropriate aTBS protocols in accordance with embodiments of the invention can reduce time to clinical improvement to days from weeks compared to conventional rTMS/TBS meaning patients can be hospitalized for shorter amounts of time.

Further, methods for performing aTBS can include generating personalized aTBS targets for TBS stimulation which take in to account the idiosyncrasies of a patient. Personalized targets can be generated for aTBS to maximize efficiency and/or efficacy of treatment for each patient. Because TMS coils are currently incapable of targeting structures deep within the brain, personalized aTBS targets can be generated to stimulate surface regions that are linked to deep regions, bypassing the need for deep brain stimulation.

The importance of proper targeting is highlighted by the critical symptoms of chronic mental illness. For example, in persons suffering from severe clinical depression, neurosurgery is considered a treatment of last resort. If treatment by implanted stimulators fails, the incidence of suicide increases dramatically. By using neuronavigation techniques described within, proper and effective targeting can be achieved prior to surgery to increase the success rate of the procedure in numerous ways. In many embodiments, aTBS is performed on a trial basis to test the efficacy of a neuronal implant prior to surgery by stimulating a selected target or set of targets. In a variety of embodiments, targets with the best test results are selected as targets for an implantable system. In the case that no target with a high enough chance of success for the patient and/or medical professionals is found, then the invasive surgery can be avoided entirely. As magnetic stimulation and electric stimulation are closely related, implanted neurostimulators can be programmed to provide electrical stimulation protocols similar to aTBS magnetic protocols with similar results. Systems for performing aTBS and neuronavigation targeting methods are discussed below.

aTBS Systems aTBS systems in accordance with embodiments of the invention can acquire neuroimaging data of a patient's brain and generate personalized aTBS targets for treatment with aTBS devices. In many embodiments, aTBS systems include aTBS devices. A conceptual diagram of an aTBS system in accordance with an embodiment of the invention is shown in FIG. 1. aTBS system 100 includes an aTBS Device 110. aTBS devices can be any TMS coil that is capable of delivering magnetic pulses with the frequencies, intensities, and durations required by aTBS. aTBS devices can be, but are not limited to, a Magventure X100 produced by MagVenture of Farum, Denmark, Magstim coils produced by The Magstim Company Limited of Whitland, United Kingdom, Neurosoft coils produced by Neurosoft of Utrecht, Netherlands, and the Brainsway H7-deep-TMS system, or the H1 Coil TMS device, both of which are produced by Brainsway Ltd. of Jerusalem, Israel. However, any TMS coil can be used as appropriate to the requirements of specific applications of embodiments of the invention. Further, aTBS systems can include more than one aTBS device in order to better target different regions of the brain.

In numerous embodiments, neuronavigation systems can be used to correctly place the aTBS device relative to the aTBS target. Neuronavigation systems capable of displaying the aTBS target can include Localite TMS Navigator produced by Localite GmbH of Sankt Augustin, Germany, visor2 systems produced by ANT Neuro of the Netherlands, and BrainSite TMS Navigation produced by Rogue Solutions Ltd. of Cardiff, Wales. However, any kind of neuronavigation device capable of assisting with the placement of the aTBS device can be utilized as appropriate to the requirements of specific applications of embodiments of the invention. In numerous embodiments, the neuronavigation system is provided and/or generates a target or set of targets generated using targeting processes described below.

aTBS system 100 further includes an aTBS computing system 120 and a brain imaging device 130. aTBS computing systems can be implemented as one or more computing devices capable of processing brain image data and generating personalized aTBS targets. Brain imaging devices are capable of obtaining imaging data describing a patient's brain. Brain imaging devices can obtain structural, functional imaging data, and/or resting state imaging data. In numerous embodiments, brain imaging devices are magnetic resonance imaging (MRI) machines, functional MRI machines (fMRI), or any other brain scanning device as appropriate to the requirements of specific applications of embodiments of the invention. Functional imaging data can be obtained by scanning a patient using an fMRI scanner or other brain imaging device, while the patient is performing specific tasks and/or is provided specific stimuli. Resting state imaging data can be obtained by scanning a patient using an fMRI scanner, or other brain imaging device while the patient is not performing any task.

Additionally, aTBS system 100 includes interface device 140. Interface devices can be, but are not limited to, computers, smart-phones, tablet computers, smart-watches, or any other type of computing interface device as appropriate to the requirements of specific applications of embodiments of the invention. In many embodiments, interface devices are used to interface with brain imaging devices, aTBS computing systems, and/or aTBS devices. In numerous embodiments, aTBS computing systems and interface devices are implemented using the same physical device. aTBS system 100 includes a network 150 connecting aTBS device 110, aTBS computing system 120, and interface device 130. In a variety of embodiments, the network is the Internet. However, any network such as, but not limited to, an intranet, a local area network, a wire area network, or any other computing network capable of connecting computing devices can be used as appropriate to the requirements of a given application.

Figure 2:
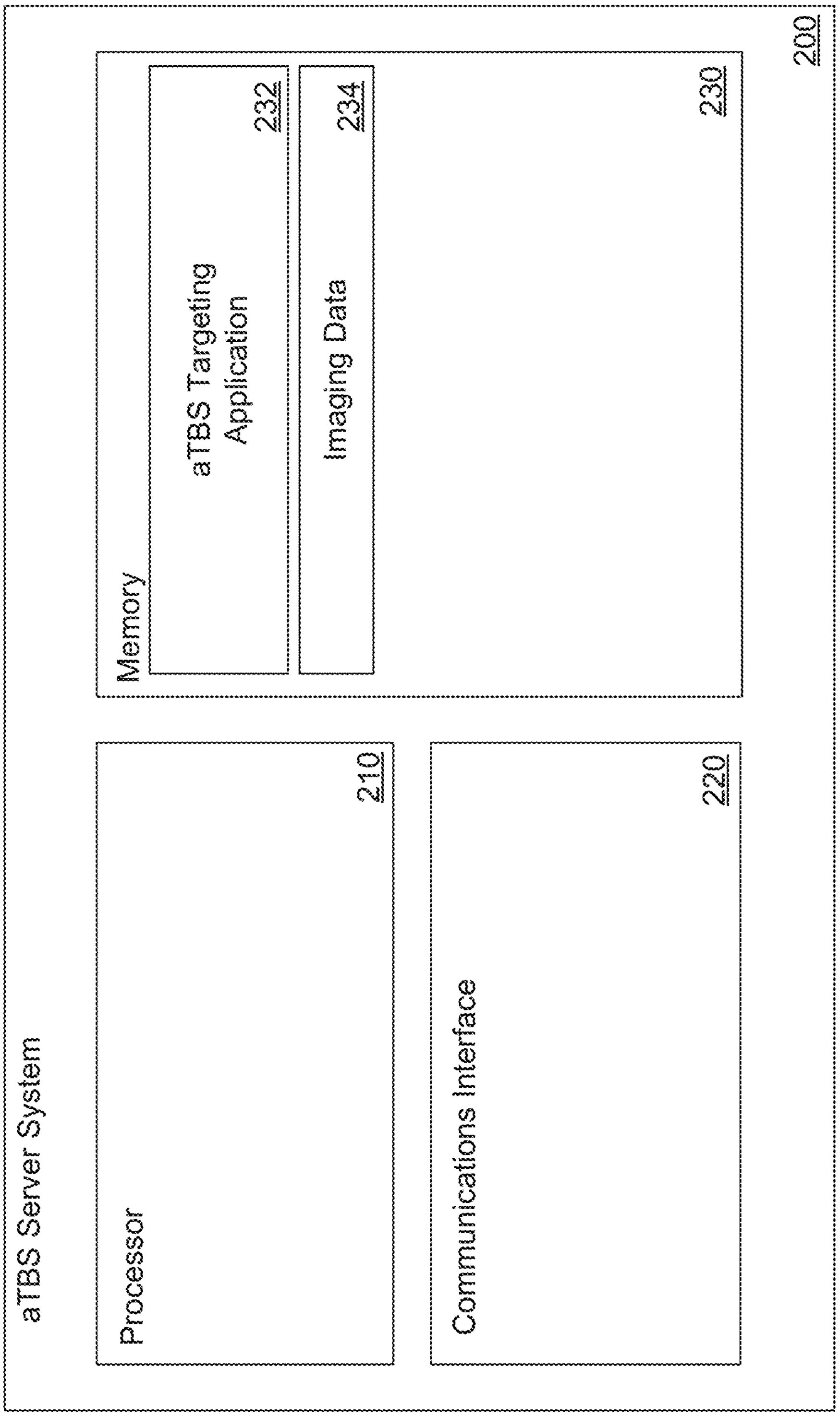
FIG. 2 is a diagram illustrating an accelerated Theta-Burst Stimulation computing system in accordance with an embodiment of the invention.

While a specific aTBS system is illustrated with respect to FIG. 1, one of ordinary skill in the art would appreciate that numerous different configurations of aTBS systems are possible, including, but not limited to, system architectures where different devices are not connected, or not all connected, by a network. aTBS computing systems are discussed below.

aTBS Computing systems aTBS computing systems in accordance with embodiments of the invention can generate personalized aTBS targets for a given patient. A conceptual illustration of an aTBS computing system in accordance with an embodiment of the invention is shown in FIG. 2. aTBS computing system 200 includes a processor 210 in communication with a communications interface 220 and a memory 230. In numerous embodiments, aTBS computing systems include multiple processors, multiple memories, and/or multiple communications interfaces. In a variety of embodiments, components of aTBS computing systems are distributed across multiple hardware platforms.

Processor 210 can be any type of computational processing unit, including, but not limited to, microprocessors, central processing units, graphical processing units, parallel processing engines, or any other type of processor as appropriate to the requirements of specific applications of embodiments of the invention. Communications interface 220 can be utilized to transmit and receive data from other aTBS computing systems, brain imaging devices, aTBS devices, and/or interface devices. Communications interfaces can include multiple ports and/or communications technologies in order to communication with various devices as appropriate to the requirements of specific applications of embodiments of the invention.

Memory 230 can be implemented using any combination of volatile and/or non-volatile memory, including, but not limited to, random access memory, read-only memory, hard disk drives, solid-state drives, flash memory, or any other memory format as appropriate to the requirements of specific applications of embodiments of the invention. In numerous embodiments, the memory 230 stores a variety of data, including, but not limited to, an aTBS targeting application 232 and imaging data 234. In many embodiments, the aTBS targeting application and/or the imaging data are received via the communications interface. Processor 210 can be directed by the aTBS targeting application to perform a variety of aTBS processes, including, but not limited to, processing imaging data and generating aTBS targets.

Although specific architectures for aTBS computing systems in accordance with embodiments of the invention are conceptually illustrated in FIG. 2, any of a variety of architectures, including, but limited to, those that direct aTBS devices to perform aTBS, direct brain imaging devices to capture imaging data, and/or utilize different hardware capable of performing similarly to the above can also be utilized. Furthermore, aTBS computing systems can be implemented on multiple servers within at least one computing system. For example, aTBS computing systems can be implemented on various remote "cloud" computing systems as appropriate to the requirements of specific applications of embodiments of the invention. However, one of ordinary skill in the art would appreciate that a "computing system" can be implemented on any appropriate computing device, including, but not limited to, a personal computer, a server, a cluster of computing devices, and/or a computing device incorporated into a medical device. In numerous embodiments, aTBS computing systems are implemented as part of an integrated aTBS device. A discussion of various aTBS processes is found below.

Processes for Performing aTBS

Traditional rTMS procedures utilize large numbers of pulses over a long period of time. Traditional TBS utilizes patterned pulses which reduce the number of pulses required to achieve similar results to rTMS. However, neither method can produce clinically useful changes in under a week. Processes for performing aTBS in accordance with embodiments of the invention can include accelerated treatment regimens compared to conventional rTMS/TBS methods.

Figure 3:
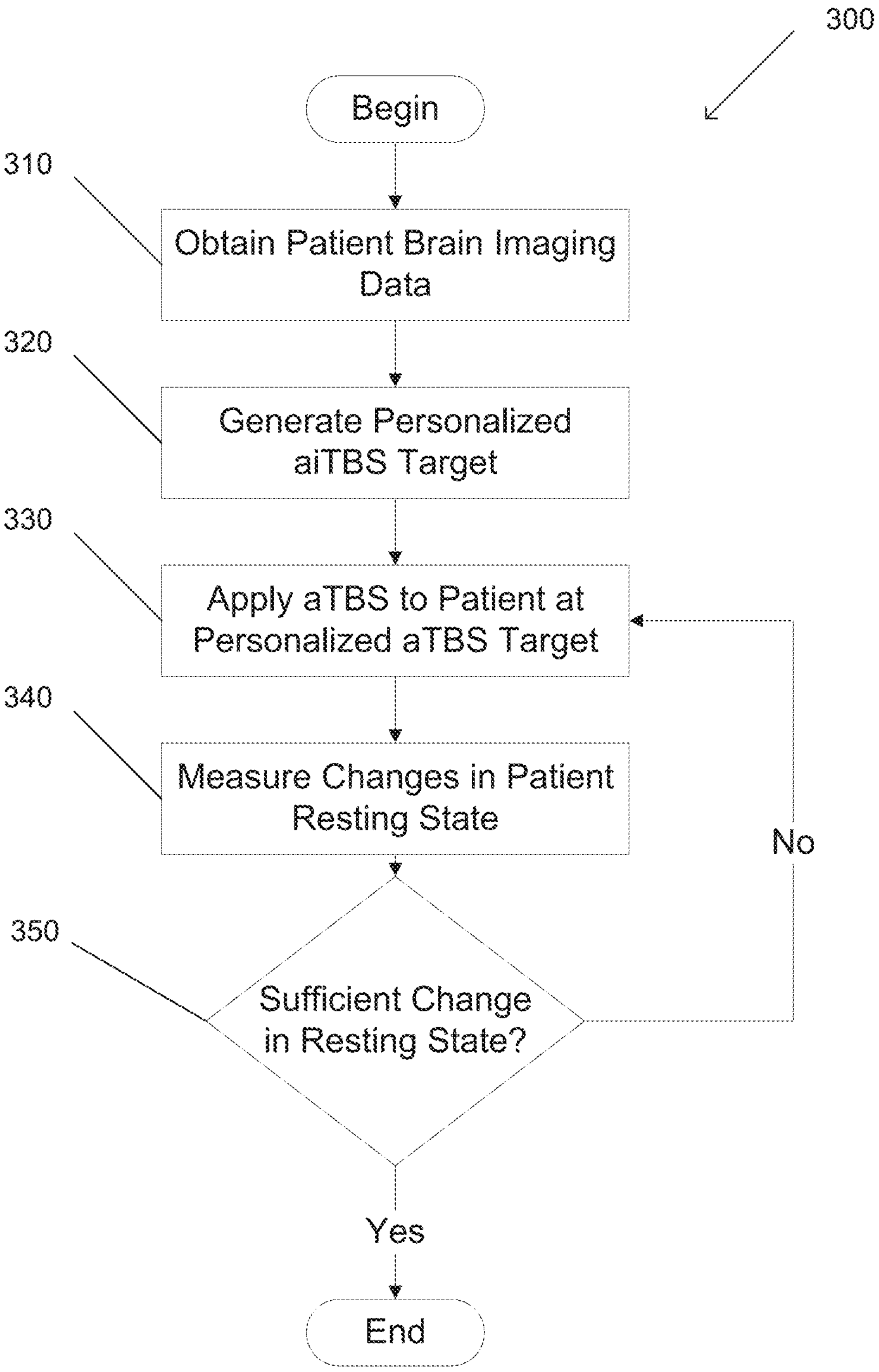
FIG. 3 is a flow chart illustrating a method for applying personalized accelerated intermittent Theta-Burst Stimulation to a patient in accordance with an embodiment of the invention.

Turning now to FIG. 3, a process for performing aTBS in accordance with an embodiment of the invention is illustrated. Process 300 includes obtaining (310) patient brain imaging data. In numerous embodiments, patient brain imaging data includes anatomical imaging data, resting state imaging data, functional imaging data, and/or any other brain imaging data as appropriate to the requirements of specific applications of embodiments of the invention. Anatomical imaging data can include, but is not limited to, structural MRI scan data, diffusion tensor imaging data, computed tomography scans, and/or any other structural image of a brain produced by an imaging technology. Functional imaging data is imaging data that describes the neuronal activation of a brain. Resting state imaging data is imaging data that describes the neuronal activation of a brain during a resting state. In numerous embodiments, functional imaging data and resting state imaging data are obtained from fMRI scans.

Patient brain imaging data can be used to generate (320) personalized aTBS targets. aTBS can be applied (330) to the patient at the personalized aTBS target. In many embodiments, the TMS coil utilized to apply the aTBS treatment is focused on the target by manipulating the placement of coil and/or the coil angle, and thus the orientation of the magnetic field. In many embodiments, aTBS is applied according to a pre-determined protocol. aTBS protocols can vary depending on numerous factors, including, but not limited to, the severity of condition, whether or not aiTBS or acTBS is used, or any other factors as appropriate to the requirements of specific applications of embodiments of the invention. aTBS protocols can include a set of parameters describing the form of iTBS to be applied, and a schedule describing when the iTBS is applied. In numerous embodiments, include e-field measurements are used to inform the choice of coil angle.

In numerous embodiments, aiTBS schedules involves applying iTBS pulses for multiple sessions per day, for several days. In a variety of embodiments, the iTBS pulse parameters involve 3-pulse, 50 Hz pulses at 5 Hz for 2 second trains, with trains every 10 seconds for 10 minute sessions (1,800 total pulses per session). In many embodiments, aiTBS schedules describe conducting 10 sessions per day with 50-minute intersession intervals for 5 consecutive days (18,000 pulses per day, 90,000 total pulses).

However, a wide range of parameters can be used, for example, iTBS pulse parameters can involve any number of pulses of between 20 Hz and 70 Hz, at 3 Hz to 7 Hz, with trains every 4 seconds to 10 seconds, with intersession intervals between 25 minutes and 120 minutes. An example schedule for treatment using aiTBS in accordance with an embodiment of the invention is illustrated in FIG. 4.

In a variety of embodiments, the cTBS pulse parameters involve 3-pulse trains with 50 Hz pulses at 5 Hz for 40 second sessions (600 total pulses per session). In a variety of embodiments, the cTBS pulse parameters involve 3-pulse, 30 Hz pulses at 6 Hz for 44 second sessions (800 total pulses per session). In many acTBS embodiments, 30 sessions are applied per day with 15-minute intersession intervals for 5 consecutive days (18,000 pulses per day, 90,000 total pulses). However, a wide range of parameters can be used, for example, cTBS parameters can involve any number of pulses of 20 Hz to 70 Hz, at 3 Hz to 7 Hz with an intersession interval of between 10 and 50 minutes. An example schedule for treatment using acTBS in accordance with an embodiment of the invention is illustrated in FIG. 5.

However, TBS parameters and schedules for an aTBS protocol can be varied. For example, the number of pulses or frequency of sessions can be increased or decreased depending on the refractoriness of the patient and/or the severity of the clinical condition (i.e. for less severe cases of depression, fewer pulses can be effectively utilized, thereby further reducing treatment times). In numerous embodiments, the number of pulses per session range from approximately 600 to 2,400 depending on the type of aTBS applied. In a variety of embodiments, the number of sessions for aiTBS range from 3 to 15 sessions per day. In many embodiments, the number of sessions for acTBS range from 10-40 sessions per day. Nonetheless, one of ordinary skill in the art would appreciate that any number of pulses and lengths of intersession intervals can be used as appropriate to the requirements of specific applications of embodiments of the invention to fit the needs of an individual patient.

Changes in the patient's resting state can be measured (340) using methods similar to those described above with respect to obtaining resting state imaging data. If there is sufficient change (350) in resting state to result in the clinical results desired, then treatment can optionally end. If there has not been a sufficient change (350) in the patient's resting state, additional aTBS treatment sessions can be performed.

Specific processes for performing aTBS in accordance with embodiments of the invention are described above and shown with respect to FIG. 3; however, any number of processes, including, but not limited to, those that use alternate number of pulses, sessions, frequencies, imaging methods, and/or degree of change in resting state, can be utilized as appropriate to the requirements of a specific application in accordance with embodiments of the invention.

Generating aTBS Targets

Figure 6:
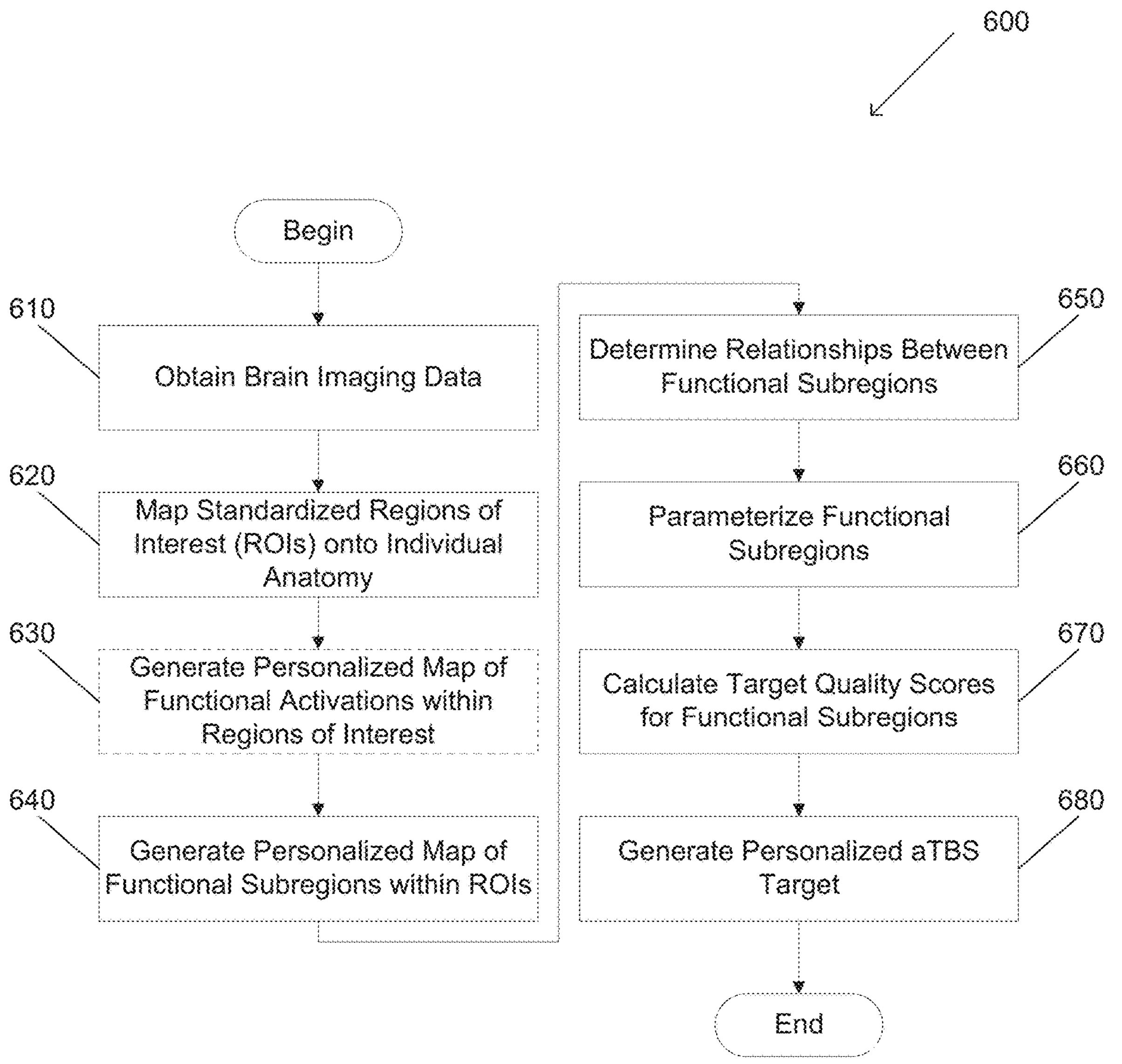
FIG. 6 is a flow chart illustrating a method for generating a personalized accelerated Theta-Burst Stimulation target in accordance with an embodiment of the invention.

Every person has a unique brain structure and connectivity. While the average across all brains has been used to generate targets, this ignores each patient's idiosyncrasies. Processes for performing aTBS in accordance with embodiments of the invention can include generating personalized aTBS targets to increase the efficiency and efficacy over standard iTBS treatment. Turning now to FIG. 6, a process for generating an aTBS target in accordance with an embodiment of the invention is illustrated.

Process 600 includes obtaining (610) brain imaging data. In many embodiments, brain imaging data includes structural imaging data, resting state imaging data, and/or functional imaging data similar to those described above. In numerous embodiments, brain imaging data is preprocessed. Preprocessing steps can include, but are not limited to, physiological noise regression, slice-time correction, motion correction, co-registration, band-pass filtering, de-trending, and/or any other preprocessing step as appropriate to the requirements of a given application. Brain imaging data can be used to map (620) standardized regions of interest (ROIs) onto the individualized anatomy. In numerous embodiments, mapping standardized regions of interest onto individualized anatomy is performed by aligning structural imaging data to a standardized brain atlas, and reversing the alignment parameters to map a standardized ROI onto an individual's anatomy. Standardized brain atlases can define one or more brain regions that are targetable with TMS. In a variety of embodiments, the brain atlas defines brain regions that are targetable with a specific TMS coil. In numerous embodiments, task-based fMRI is used to restrict and/or broaden the extent of the brain regions that are to be targeted with TMS.

In many embodiments, a personalized map of functional activations within ROIs is generated (630). In a variety of embodiments, functional activations within ROIs are identified using functional imaging data and/or resting state imaging data. The map of individualized ROIs and resting state imaging data can be used to generate (640) a personalized map of functional subregions within ROIs. In numerous embodiments, functional subregion is defined as a brain region within ROIs in which all temporal brain activity is highly correlated across the spatial extent of the subregion. In many embodiments, the resting state imaging data can be used to generate resting state functional connectivity data describing the functional connectivities between regions of the brain. In numerous embodiments, resting state data extracted from the resting state imaging data such as, but not limited to, functional connectivities and task based neuronal activations can be mapped to the personalized regions of interest. In numerous embodiments, a personalized map of task based functional activations within the ROIs can be utilized to refine or expand a functional connectivity based personalized map of functional subregions. Task-based functional imaging data can lead to more refined and/or higher quality analysis of functional connectivities between subregions.

Additionally, resting state functional connectivity data across ROIs can be further parcellated into functional subregions such that each parcellated subregion is made up of homogeneous brain activity as measured over the course of a resting state scan. In numerous embodiments, parcellation is achieved using hierarchical clustering, such as, but not limited to, hierarchical agglomerative clustering. However, any parcellation method can be used as appropriate to the requirements of a given embodiment. In a variety of embodiments, the size of a subregion is determined by the number of voxels that act in a homogenous fashion. As such, the size of a subregion can vary across different ROIs depending on the function of the subregion, the structure of the brain in which the subregion is located, the idiosyncrasies of the patient's brain, and any of a number of other factors that impact the connectivity and reactivity of the brain.

The relationships between the functional subregions can be determined (650) using a variety of techniques. In numerous embodiments, the voxel time course that is most highly correlated with the median of all voxel time courses within a functional subregion can be selected as reflecting the activity of the functional subregion. In many embodiments, taking a simple average of all time courses for voxels within the subregion can be used, although this tends to be less robust. By reducing each functional subregion to a single time course, an accurate representation of the typical time course of brain activity that occurs within groups of homogenous voxels can be determined.

Figure 7:
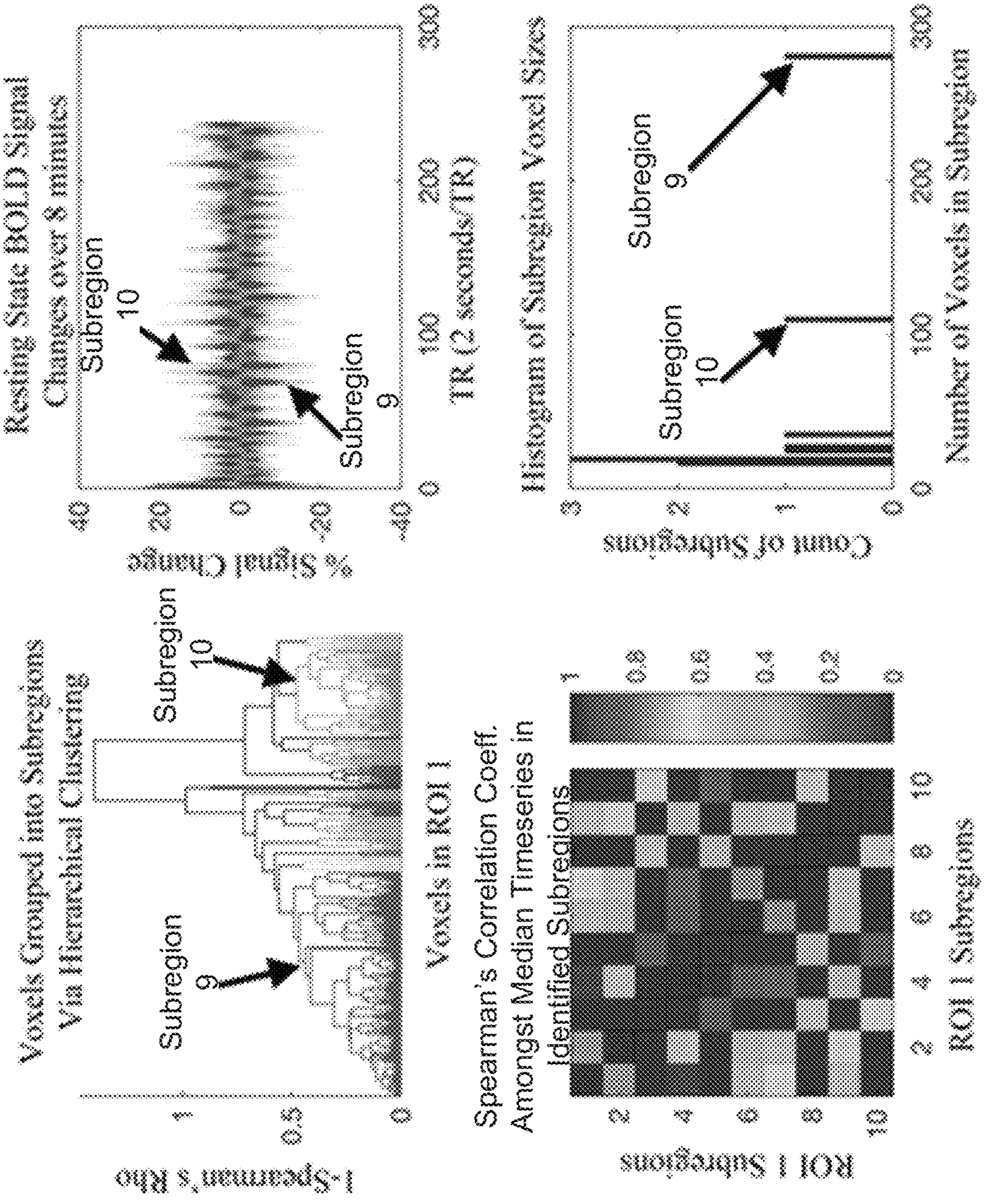
FIG. 7 is a set of charts illustrating a hierarchical agglomerative clustering algorithm for identifying functional subregions in a region of interest in accordance with an embodiment of the invention.
Figure 8A:
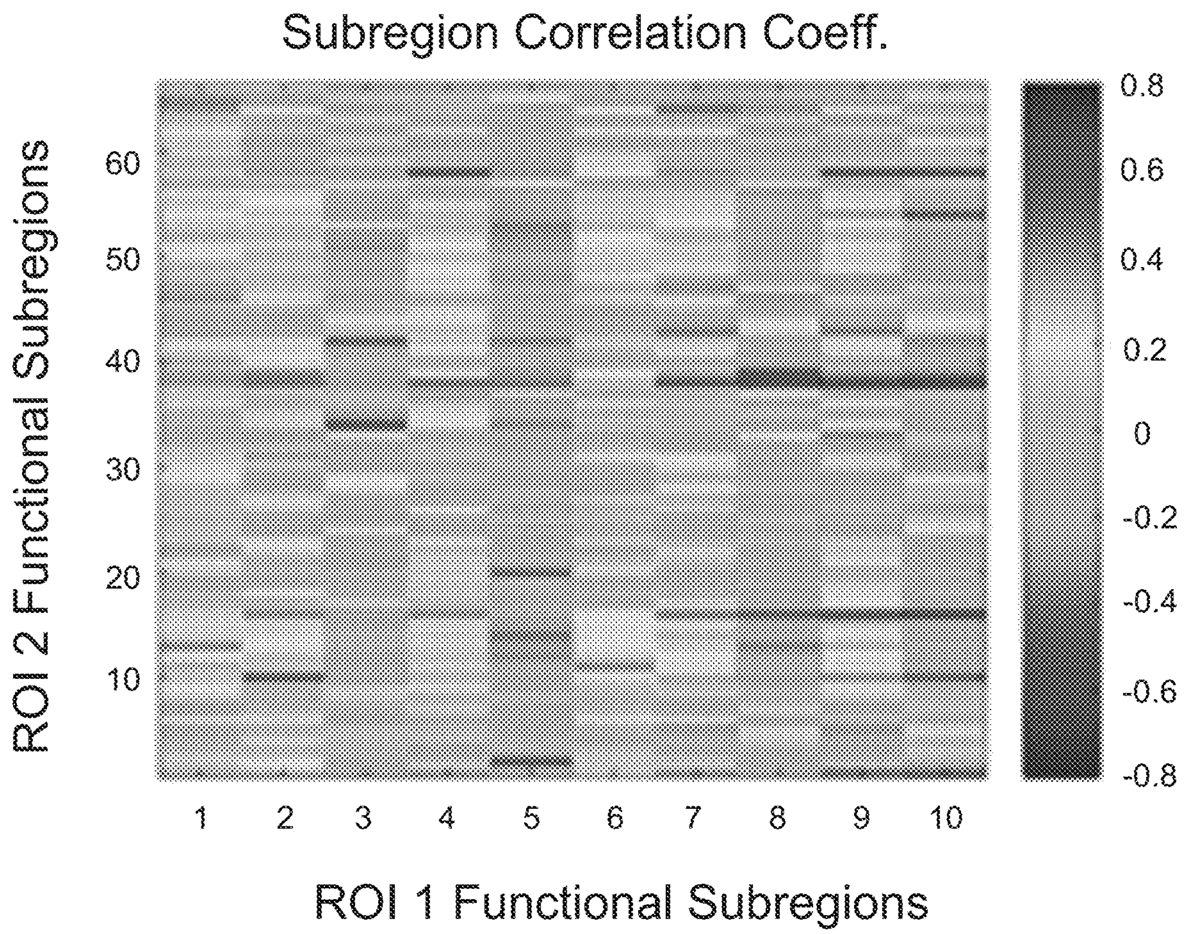
FIG. 8A is a chart of subregion correlation coefficients in accordance with an embodiment of the invention.
Figure 8B:
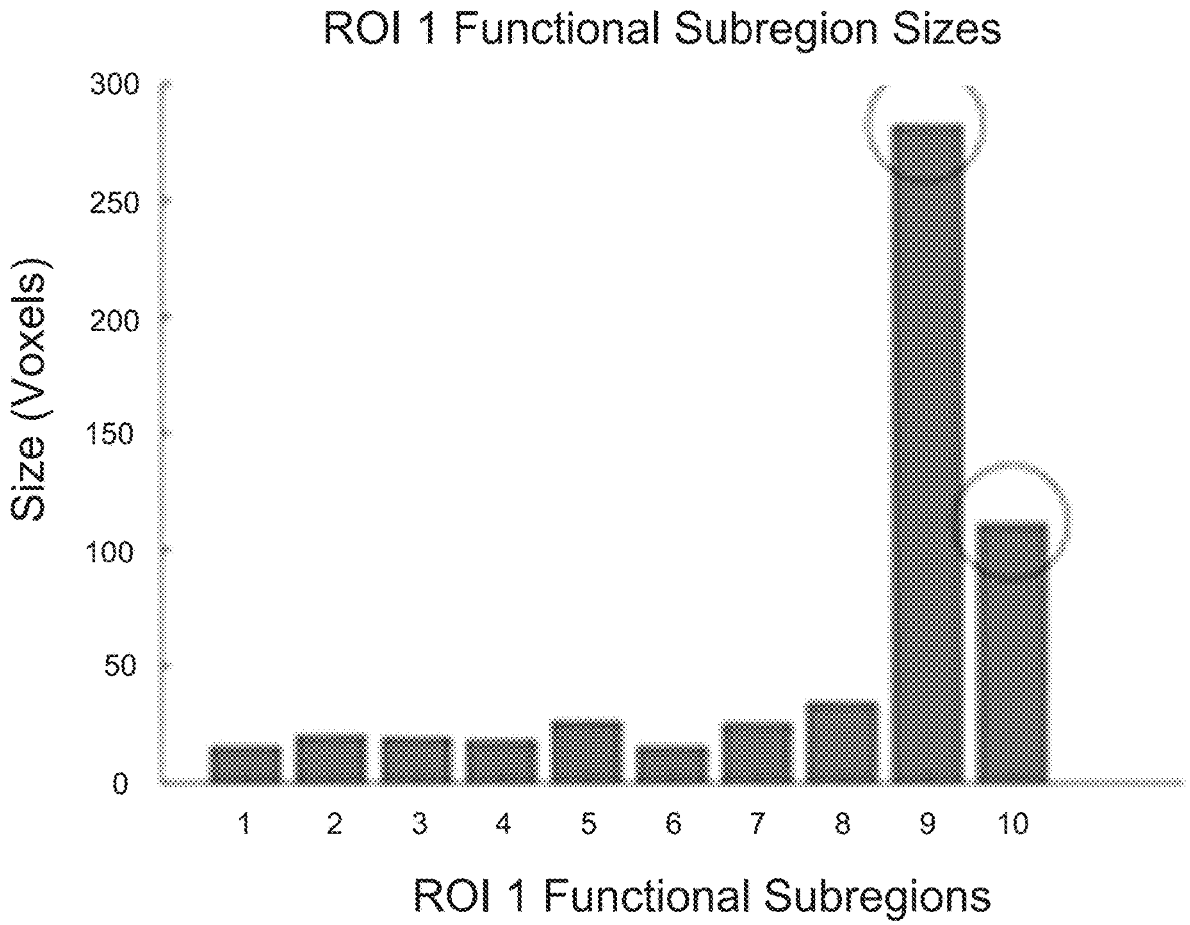
FIG. 8B is a chart of ROI 1 functional subregion sizes in accordance with an embodiment of the invention.
Figure 8C:
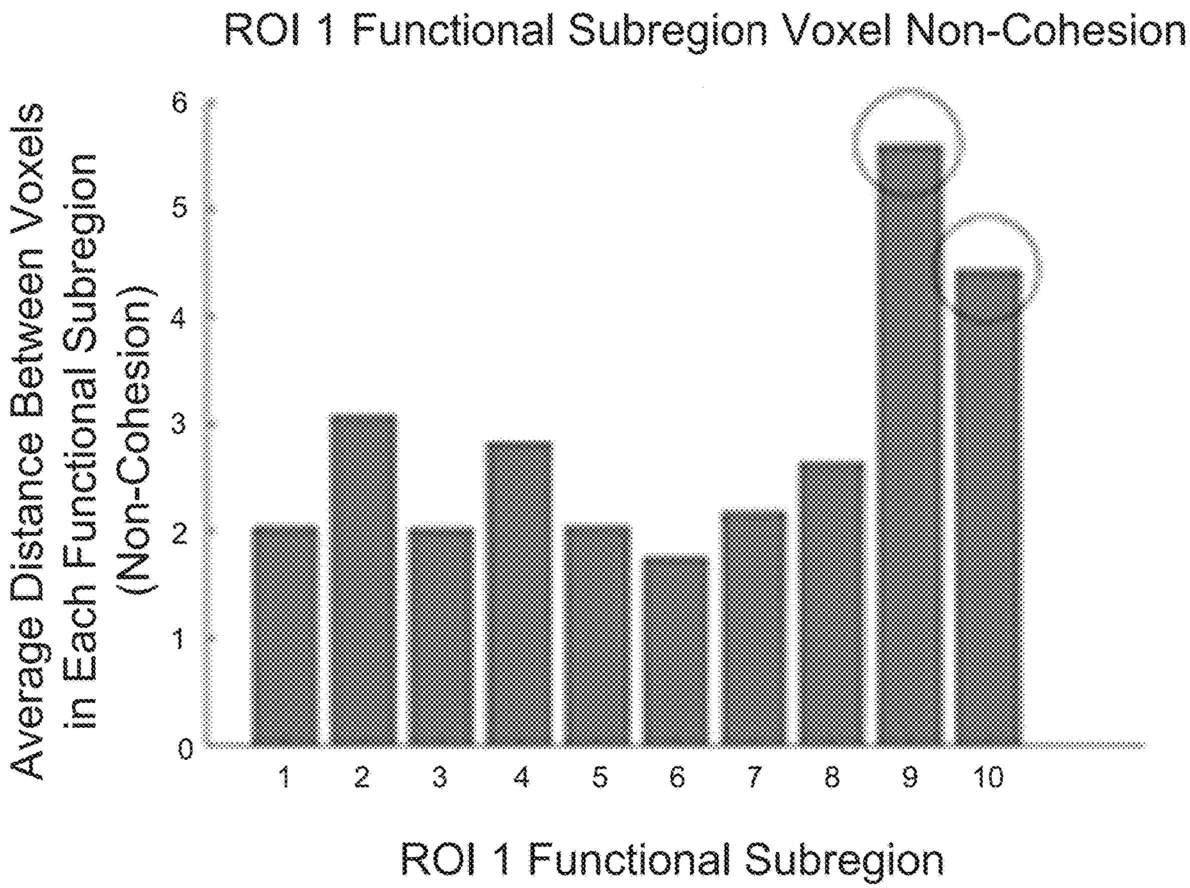
FIG. 8C is a chart of ROI 1 functional subregion voxel non-cohesion in accordance with an embodiment of the invention.
Figure 8D:
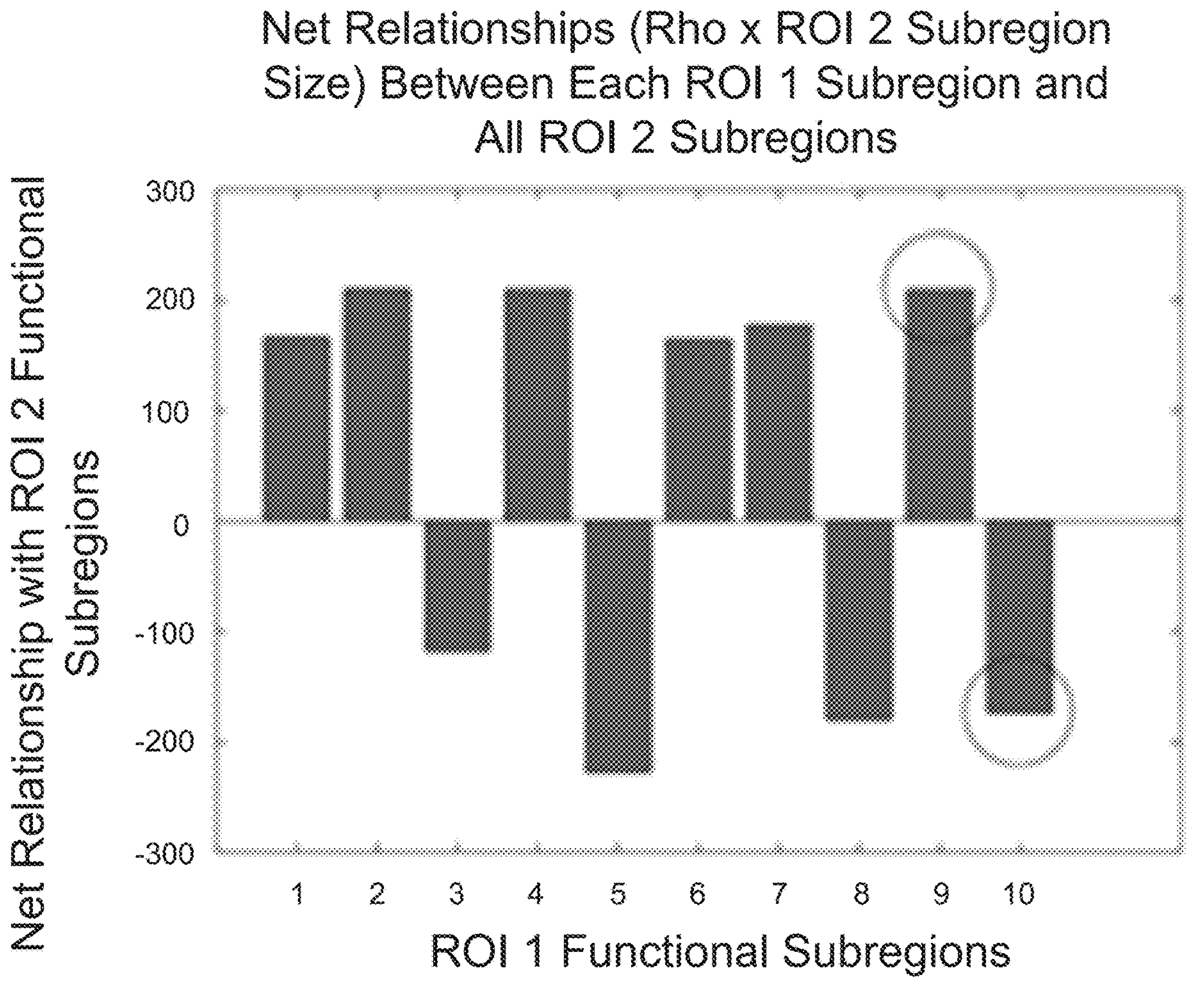
FIG. 8D is a chart of net relationships between each ROI 1 subregion an all ROI 2 subregions in accordance with an embodiment of the invention.
Figure 8E:
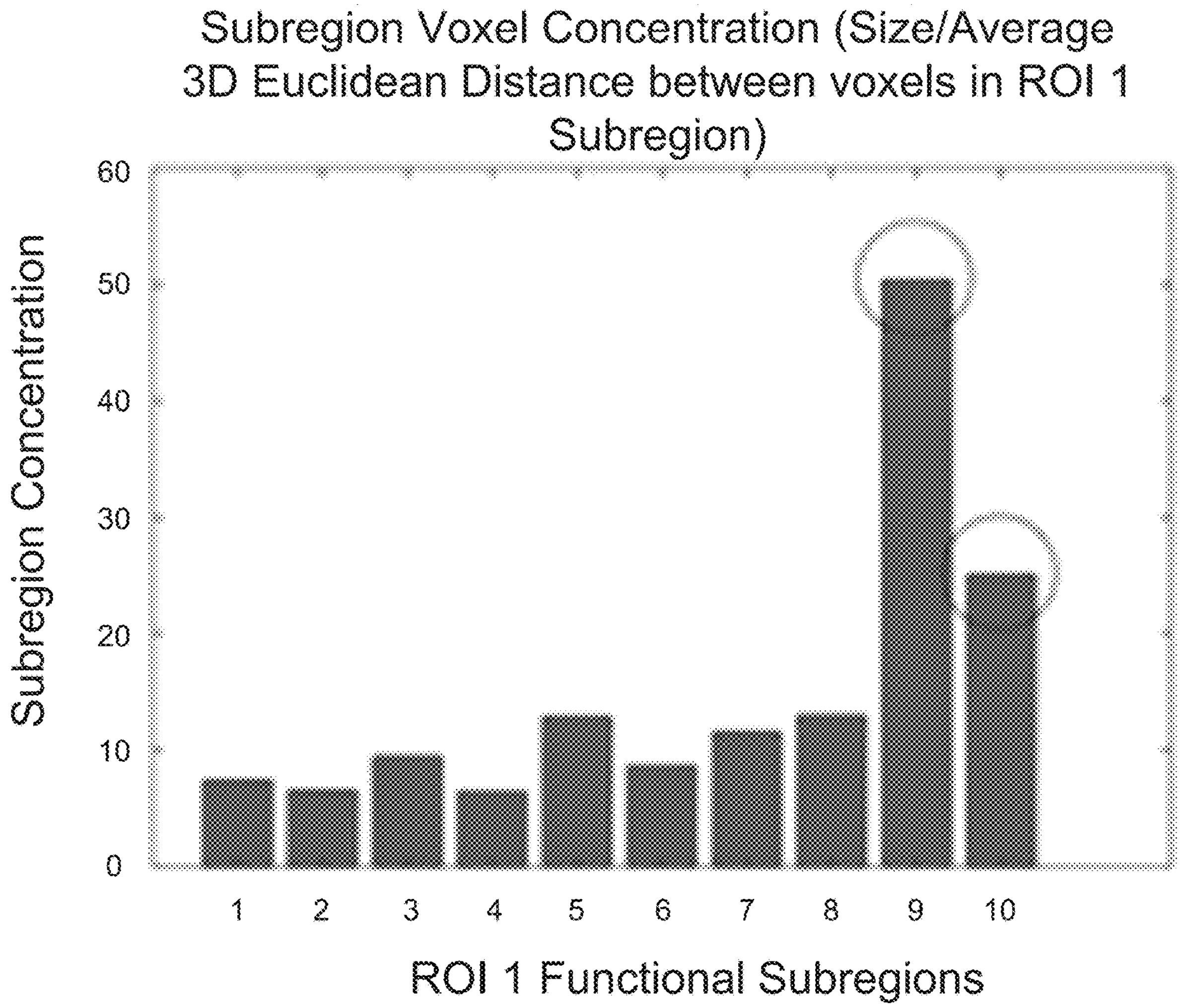
FIG. 8E is a chart of subregion voxel concentration in accordance with an embodiment of the invention.
Figure 8F:
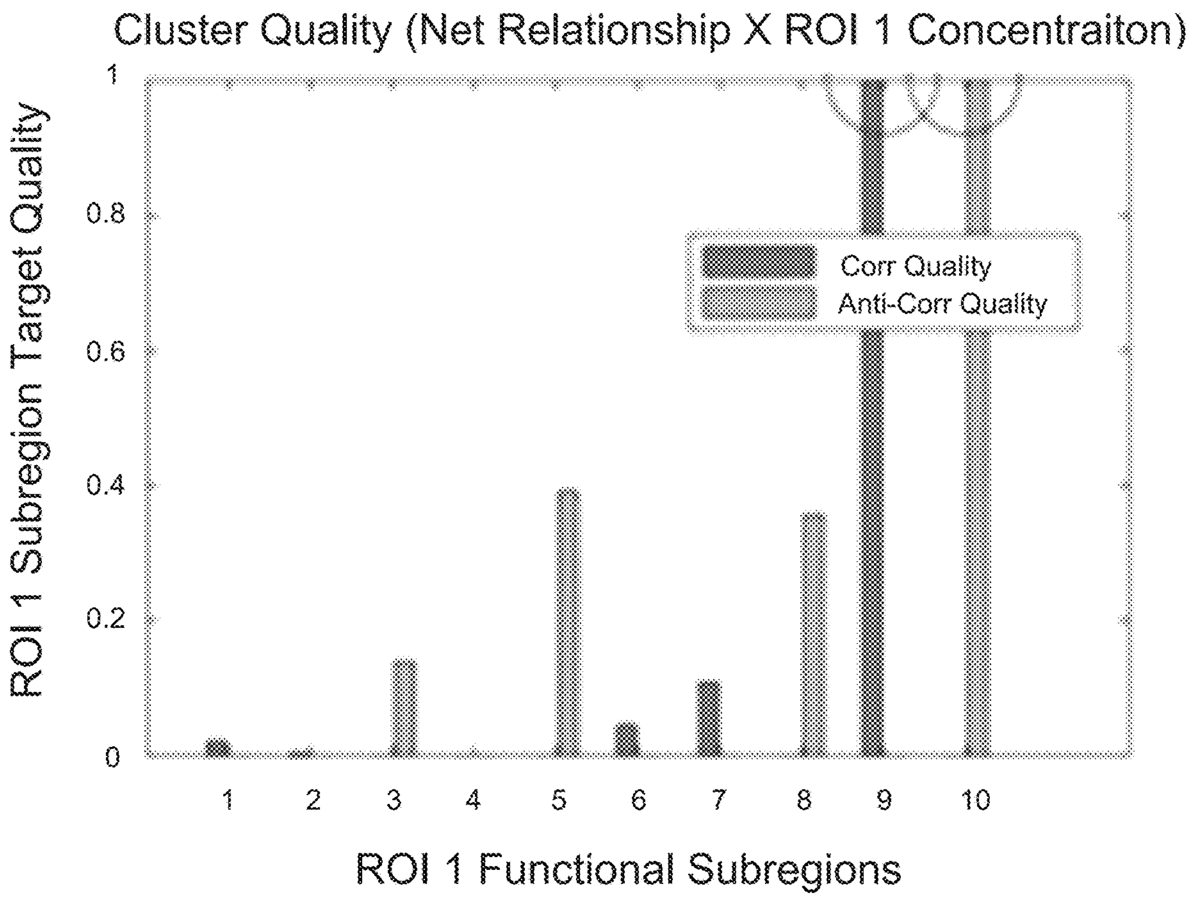
FIG. 8F is a chart of cluster quality in accordance with an embodiment of the invention.

An example grouping and correlation calculation in accordance with an embodiment of the invention is illustrated in FIG. 7. Further, single, representative time courses enable the calculation of correlation coefficients between functional subregions that exist within the same ROI. However, these correlation coefficients will tend to be low because groups of voxels with high correlation coefficients tend to be organized into the same subregion. The process of reducing each functional subregion identified through parcellation to a single time course further allows for the calculation of correlation coefficients between all functional subregions discovered across multiple ROIs across the brain. For example, multiple subregions within the left dorsolateral prefrontal cortex can be correlated with multiple subregions within the cingulate cortex, although any number of different subregions within any number of different brain structures can be correlated. An example set of correlations across multiple ROIs in accordance with an embodiment of the invention is illustrated in FIGS. 8A-8F.

Process 600 further includes parameterizing (660) functional subregions. Subregions can be assigned values for various parameters such as, but not limited to, size of the subregion i.e. the number of voxels or volume of brain, the spatial concentration of voxels i.e. the number of voxels divided by the average Euclidean 3 dimensional spatial distance between all voxels that make up the subregion, the functional relationships between a given subregion and other functional subregions (i.e. voxel-weighted average correlation coefficients), and/or accessibility of the subregion from the surface of the brain such as, but not limited to, the depth of the subregion and/or whether or not the subregion is obscured by another subregion. However, any number of parameters, or parameter weighting schemes can be used as appropriate to the requirements of a given application.

Functional subregion parameters can be used to calculate (670) target quality scores for each the functional subregions. In numerous embodiments, the target quality score for each subregion is a function of weighted combinations of subregion parameters. In many embodiments, the target quality scores are generated by determining the surface influence (voxel size-weighted correlation coefficients) for a set of subregions. In many embodiments, the surface influence for a given subregion is the sum of a two-dimensional matrix of Spearman's or Pearson's correlation coefficients derived from a hierarchical clustering algorithm describing the correlation coefficients between a surface ROI subregion and all of the deep ROI subregions. In numerous embodiments, the first ROI is located near the surface of the brain, and the second ROI is located deeper within the brain tissue. However, difference in depth is not a requirement for ROI comparisons. Surface ROI subregions that have positive influence on deep subregions and surface ROI subregions that have negative influence on deep subregions can be determined based on the surface influence calculations. In some embodiments, depending on the type of treatment, only positive or only negative influencing subregions may be further considered as targets. In numerous embodiments, the surface subregion concentration can be calculated. In many embodiments, surface subregion concentration can be calculated by dividing the number of voxels in a surface subregion by the surface subregion non-cohesion as measured by the average Euclidian distance between voxels in the subregion. The surface subregion concentration can be further normalized to assist in interpretation. In numerous embodiments, target quality scores are determined by multiplying the surface subregion concentration by the surface influence of a particular subregion. As such, target quality scores can reflect both the potential impact of stimulating a given surface subregion on a deep subregion as well as the ability and efficiency with which the subregion can be targeted by the TMS coil. However, any number of methods can be used to generate target quality scores as appropriate to the requirements of specific applications of embodiments of the invention.

Personalized aTBS target can be generated (680) based on the target quality scores. In numerous embodiments, the highest quality targets are selected as the personalized aTBS target. In a variety of embodiments, more than one target can be selected.

Specific processes for generating aTBS targets in accordance with embodiments of the invention are described above and shown with respect to FIG. 6; however, any number of processes, including, but not limited to, those that use different and/or fewer types of imaging data, use different subregion parameters, different parcellation methods, and/or any other quality generation method can be utilized as appropriate to the requirements of a specific application in accordance with embodiments of the invention.

Clinical Treatment Using aTBS

Clinical evaluation as determined that aTBS can be used to treat a variety of different medical conditions, both mental and physical. For example, aiTBS is effective at reducing suicide ideation and lessening symptoms of depression when performed over the left dorsolateral prefrontal cortex (L-DLPFC). Patients undergoing aiTBS over L-DLPFC treatment are often able to be released from hospitalization in between 2 and 5 days. Further, aiTBS over L-DLPFC can be used to increase heart rate variability, which is correlated with numerous psychiatric conditions as well as various types of cancer, various heart diseases, and inflammatory conditions.

In a variety of embodiments, heart rate variability is treated by targeting the L-DLPFC in such a way as to effect changes in the Subcallosal Cingulate Cortex (SCC) which in turn can effect changes in the vagus nerve which can be used to effect heart rate. Heart rate variability can be used as a neurophysiological biomarker that is treatment-responsive for resolution of prefrontal dysregulation of sympathetic/parasympathetic balance. For example, in many embodiments, heart rate decelerations are used to confirm target engagement. Similarly, ongoing recording of heart rate decelerations can be used for ongoing target confirmation. Identified functional subregions can be used to find the best available targets for influencing heart rate variability. This can be done by iteratively testing each functional subregion with in an ROI TMS stimulation for its effects on heart rate or heart rate variability. Implantable aTBS In numerous embodiments, for severe clinical conditions, aTBS can be applied by implanted neurostimulators. aTBS protocols can be adapted to electrical stimulation instead of magnetic stimulation, and stimuli can be applied long-term without the need for external magnetic stimulation. Further, external aTBS with an rTMS device can be performed to probe for the correct target choice and therapeutic efficacy, and then neurostimulators can be implanted over the target determined to have the most likely positive results either epidurally or subdurally. In numerous embodiments, neurostimulators provide stimulation and record brain activity. By providing both stimulation and recording channels, a closed loop system can be achieved. Based on recorded brain activity, stimulation can be modulated to either increase or decrease the amount of aTBS provided or change stimulation target. Further, machine learning algorithms can be used to adapt to the optimal stimulation strategy for that person. For example, if positive neurological activity is recorded, stimulation can cease until pathological neurological activity is detected. In numerous embodiments, recording brain activity is achieved using standard electrocortiocographical (ECoG) methods.

In a variety of embodiments, multiple stimulation electrodes can be implanted over multiple targets, either for aTBS applications or otherwise. Recording activity can be used to selectively activate or deactivate different electrodes in response to different responses for safety reasons as well as clinical as for aTBS applications. For example, if a seizure activity is detected in a particular area of the brain, stimulation electrodes in that region can be deactivated and/or utilized to induce normal brain activity.

Neurostimulators can also be used with open loop parameters, where a static protocol is utilized to maintain a desired brain activation pattern. In many embodiments, the static protocol can be adapted or modified via an external controller. Many neurostimulator devices use a combination of open loop and/or closed looped formats as appropriate to the requirements of a given application of an embodiment of the invention.

As noted above, neurostimulators can be placed on targets selected using neuronavigation techniques above. However, when the surgeon is placing the neurostimulator, it can be useful to verify placement during the procedure. In numerous embodiments, organ responses to brain stimulation can be used to verify placement. For example, an electrode placed on the L-DLPFC can affect heart rate, and by measuring heart rate, stimulation of the L-DLPFC can be verified. As L-DLPFC stimulation can also effect depression, this can be a useful clinical tool for implantation of neurostimulators to treat clinical depression.

Electrocorticography (epidural/subdural), EEG, and NIRS can be correlated with heart rate and heart rate variability, and both can be used as closed loop indicators of ongoing efficacious stimulation.

Further, as aTBS is able to be performed to have an excitatory (aiTBS) or an inhibitory (acTBS) effect, with correct target selection, various neurological changes can be implemented that can have impacts beyond the brain. For example, manipulating the hypothalamus can impact cortisol secretion by altering the hypothalamic-pituitary-adrenal axis. Additionally, post-injury, neurological plasticity can be increased by exciting and inhibiting different neuronal connections. Similarly, aTBS can be used to promote learning and skill acquisition by increasing neurological plasticity directly in targeted neuronal networks or elsewhere.

Although specific systems and methods for performing aTBS are discussed above, many different systems and methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents. U.S. patent application Ser. No. 16/215,475 titled "Systems and Methods for Clinical Neuronavigation" filed Dec. 10, 2018, and U.S. patent application Ser. No. 16/215,512 titled "Systems and Methods for Personalized Clinical Applications of Accelerated Theta-Burst Stimulation" filed Dec. 10, 2018 are incorporated by reference in their entireties herein for all purposes.

What is claimed is:

1. A method for treating neurological conditions, comprising:

implanting a neurostimulator over a target structure of a patient's brain; and applying accelerated intermittent theta burst stimulation (aiTBS) to the target structure using the neurostimulator during a plurality of sessions on a given day in order to treat a neurological condition;

where each session in the plurality of sessions is separated by an intersession interval lasting between 25 and 120 minutes during which no neurostimulation is applied; and during each session in the plurality of sessions, the neurostimulator is configured to provide the aiTBS by generating a plurality of pulse trains that each comprise a set of pulses, where each set of pulses is separated by an intertrain interval.

2. The method of claim 1, wherein each pulse in each set of pulses is between 20 Hz and 70 Hz, and pulses in each set of pulses are applied at between 3 Hz to 7 Hz.

3. The method of claim 1, wherein the intertrain interval lasts between 4 to 10 seconds; and wherein each session in the plurality of sessions lasts between 3 and 15 minutes.

4. The method of claim 1, wherein the plurality of sessions comprises between 3 and 15 sessions.

5. The method of claim 1, wherein each pulse train in the plurality of pulse train lasts for 2 seconds; and wherein each pulse train in the plurality of pulse trains comprises pulses in the form of three, 50 Hz pulses applied at 5 Hz, where the intertrain interval is 10 seconds; and wherein the plurality of sessions comprises at least ten, 10-minute sessions; and wherein the intersession interval is 50 minutes.

6. The method of claim 1, wherein the neurological condition is clinical depression.

7. The method of claim 1, wherein the neurological condition is suicidal ideation.

8. The method of claim 1, wherein the aiTBS comprises magnetic neurostimulation.

9. The method of claim 1, wherein the aiTBS comprises electric neurostimulation.

10. A method for treating neurological conditions, comprising:

implanting a neurostimulator over a target structure of a patient's brain; and applying accelerated continuous theta burst stimulation (acTBS) to the target structure using the neurostimulator during a plurality of sessions on a given day in order to treat a neurological condition;

where each session in the plurality of sessions is separated by an intersession interval lasting between 10 and 50 minutes during which no neurostimulation is applied; and during each session in the plurality of sessions, the neurostimulator is configured to provide the acTBS by generating a plurality of pulse trains that each comprise a set of pulses.

11. The method of claim 10, wherein each pulse in each set of pulses is between 20 Hz to 70 Hz, and pulses in each set of pulses are applied at between 3 Hz to 7 Hz; and wherein each session in the plurality of sessions lasts between 40 and 44 seconds.

12. The method of claim 10, wherein the plurality of sessions comprises between 10 and 40 sessions.

13. The method of claim 10, wherein each session in the plurality of sessions for a given day comprises a set of 3-pulse trains, where each pulse is 50 Hz applied at 5 Hz; and wherein each session in the plurality of sessions lasts 40 seconds.

14. The method of claim 10, wherein the plurality of pulse trains comprises three-pulse trains, where each pulse in each three-pulse train is 30 Hz;

wherein pulses in each three-pulse train are applied at 6 Hz; and wherein each session in the plurality of sessions lasts 44 seconds.

15. The method of claim 10, wherein the neurological condition is clinical depression.

16. The method of claim 10, wherein the neurological condition is suicidal ideation.

17. The method of claim 10, wherein the acTBS comprises magnetic neurostimulation.

18. The method of claim 10, wherein the acTBS comprises electric neurostimulation.

* * * * *